United States Patent [19]
Höök et al.

[11] Patent Number: 5,866,541
[45] Date of Patent: Feb. 2, 1999

[54] FIBRONECTION BINDING PROTEIN FROM *STREPTOCOCCUS DYSGALACTIAE*

[75] Inventors: Magnus Höök, Birmingham, Ala.; Kjell Martin Lindberg, Upsala, Sweden; Per-Eric Lindgren, Upsala, Sweden; Lars Christer Signäs, Upsala, Sweden

[73] Assignee: Alfa-Laval Agri International Aktiebolag, Tumba, Sweden

[21] Appl. No.: 428,713

[22] Filed: Apr. 25, 1995

Related U.S. Application Data

[62] Division of Ser. No. 125,222, Sep. 23, 1993, Pat. No. 5,416,021, which is a continuation of Ser. No. 973,551, Nov. 9, 1992, abandoned, which is a continuation of Ser. No. 352,949, May 17, 1989, abandoned.

[30] Foreign Application Priority Data

May 20, 1988 [SE] Sweden .................................. 8801894

[51] Int. Cl.$^6$ .......................... A61K 38/16; C07K 14/315
[52] U.S. Cl. .............................. 514/12; 530/324; 530/350
[58] Field of Search ........................ 514/2, 12; 530/324, 530/350

[56] References Cited

U.S. PATENT DOCUMENTS

| | | | |
|---|---|---|---|
| 3,917,818 | 11/1975 | Botes | 424/163.1 |
| 4,312,942 | 1/1982 | Blobel et al. | 435/7.24 |
| 4,425,330 | 1/1984 | Norcross et al. | 424/203.1 |
| 4,645,757 | 2/1987 | Hjerten et al. | 514/54 |
| 4,784,989 | 11/1988 | Hook et al. | 514/21 |
| 4,795,803 | 1/1989 | Lindberg et al. | 530/324 |
| 5,189,015 | 2/1993 | Höök et al. | 424/243.1 |

FOREIGN PATENT DOCUMENTS

| | | |
|---|---|---|
| 0163623 | 12/1985 | European Pat. Off. |
| 0294349 | 12/1988 | European Pat. Off. |
| 0342173 | 11/1989 | European Pat. Off. |
| 0343137 | 11/1989 | European Pat. Off. |
| 0397633 | 11/1990 | European Pat. Off. |
| WO-85/05037 | 11/1985 | WIPO . |
| WO 85/05553 | 12/1985 | WIPO . |
| WO 92/02555 | 2/1992 | WIPO . |

OTHER PUBLICATIONS

Overbeeke et al. —*J. Mol. Biol.* 163:513–532 (1983).
Raja et al. —*Infect. Immun.* 58(8):2593–8 (1990).
Ryden et al. —*J. Biol. Chem.* 258(5):3396–3401 (Mar. 1983).
Sambrook et al. —*Molecular Cloning: a Laboratory Manuel*, (2d), 6.39–6.43, B.9 (1989).
Signas et al. —*Proc. Natl. Acad. Sci.* 86:699–703 (1989).
Switalski et al. —*Eur. J. Clin. Microbiol.* 1:381–387 (1982).
Abrahmsen et al. —*Nucl. Acid Res.* 14(18):7487–7500 (1986).
Chhatwal et al. —*Comp. Immunol. Microbiol. Infect. Dis.* 1092):99–108 Abstract (1987).
Duggleby et al. —*Nuc. Acis. Res.* 11(10):3065–3076 (1983).
Espersen et al. —*Infect. and Immun.* 37(2):526–531 (Aug. 1982).
Flock et al. —*EMBO J.* 6(8):2351–2357 (1987).
Froman et al. —*J. Biol. Chem.* 262(14):6564–6571 (1987).
Keil–Dlouha et al. —*Biochem. Biophys. Acta.* 727:115–21 (1983).
Lofdahl al. —*Proc. Natl. Acad. Sci.* 80:697–701 (Feb. 1983).
Mamo et al. —*Micro. Pathog.* 2(6):417–424 Abstract (1987).
McGavin et al. —*J. Biol. Chem.* 266(13):8343–7 (1991).
Myhre—*J. Med. Microbiol.* 18(2):189–196 Abstract (1984).
Myhre et al. —*Infect Immun.* 40(1):29–34 (1983).
Nuesch et al. —*Gene* 32:243–249 (1984).

*Primary Examiner*—Stephen Walsh
*Assistant Examiner*—Karen E. Brown
*Attorney, Agent, or Firm*—Burns, Doane, Swecker & Mathis

[57] ABSTRACT

The present invention relates to new recombinant DNA-molecules comprising nucleotide sequences of *S. dysgalactiae* encoding for at least one protein or polypeptide having fibronectin binding property.

10 Claims, 8 Drawing Sheets

FIG. 3A pSDF102

```
A1  EDTQTSQEDI  V-LGGPGQVI  DFTEDSQPGM  SGNNSHTT
    ||   ||||   |  || ||||  ||||| | ||  || ||||
A2  EDSKPSQEDE  VIIGGQGQVI  DFTEDTQSGM  SGDNSHTDG  TVLE
    ||||||||||  ||||||||||  ||||||| ||  || ||
A3  EDSKPSQEDE  VIIGGQGQVI  DFTEDTQTGM  SGAGQVESP
       |  |||     |  |  |||    ||  ||     |
    TITEETHKPE  IIMGGQSDPI  DMVEDTLPGM  SGSNEAEDT
```

FIG. 3B pSDF203

```
A1  EETLPTEQGQ  SGSTTEVEDT  KGPEVIIGGQ  GEIVDI
    || ||||||||  ||||||||||  ||||||||||  || |||
A2  EENLPTEQGQ  SGSTTEVEDT  KGPEVIIGGQ  GEVVDI
    || ||||||||  |||||||||      |           |
A3  EESLPTEQGQ  SGSTTEVEDS  KPKLSIHFDN  EWPKED
```

FIG. 4

```
  1 ----------+-- --------+---- -----+------ ---+--------  48
    CTAGATACCTCA GAAAACAAAAAA TCTGTAACTGAA AAAGTAATAACT
    LeuAspThrSer GluAsnLysLys SerValThrGlu LysValIleThr
 49 -+---------+ ----------+-- -------+---- -----+------  96
    AGCGATGTTAAA TATAAGATTAAT GATAAAGAAGTG AAAGGTAAAGAA
    SerAspValLys TyrLysIleAsn AspLysGluVal LysGlyLysGlu
 97 ---+-------- -+---------+ ----------+-- -------+---- 144
    CTAGACGATGTC TCTTTAACTTAC AGTAAAGAAACC GTTCGTAAGCCA
    LeuAspAspVal SerLeuThrTyr SerLysGluThr ValArgLysPro
145 -----+------ ---+-------- -+---------+ ----------+-- 192
    CAGGTGGAACCA AATGTTCCTGAT ACACCTCAGGAA AAACCATTGACA
    GlnValGluPro AsnValProAsp ThrProGlnGlu LysProLeuThr
193 --------+---- -----+------ ---+-------- -+---------+ 240
    CCGCTTGCACCG TCAGAACCTTCA CAACCATCTATT CCAGAGACACCA
    ProLeuAlaPro SerGluProSer GlnProSerIle ProGluThrPro
241 ----------+-- --------+---- -----+------ ---+-------- 288
    CTGATACCGTCA GAACCTTCAGTT CCAGAGACATCA ACACCAGAAGGT
    LeuIleProSer GluProSerVal ProGluThrSer ThrProGluGly
289 -+---------+ ----------+-- -------+---- -----+------ 336
    CCAACAGAGGGA GAAAATAATCTT GGTGGTCAGAGT GAAGAGATAACG
    ProThrGluGly GluAsnAsnLeu GlyGlyGlnSer GluGluIleThr
337 ---+-------- -+---------+ ----------+-- -------+---- 384
    ATTACAGAAGAT TCTCAATCAGGG ATGTCTGGTCAA AATCCTGGTTCT
    IleThrGluAsp SerGlnSerGly MetSerGlyGln AsnProGlySer
385 -----+------ ---+-------- -+---------+ ----------+-- 432
    GGAAATGAAACA GTGGTTGAAGAC ACTCAAACAAGT CAAGAGGATATT
    GlyAsnGluThr ValValGluAsp ThrGlnThrSer GlnGluAspIle
433 --------+---- -----+------ ---+-------- -+---------+ 480
    GTACTTGGTGGT CCAGGTCAAGTG ATTGACTTTACA GAAGATAGCCAA
    ValLeuGlyGly ProGlyGlnVal IleAspPheThr GluAspSerGln
481 ----------+-- --------+---- -----+------ ---+-------- 528
    CCGGGTATGTCT GGTAATAATAGC CATACTATTACA GAAGATTCTAAA
    ProGlyMetSer GlyAsnAsnSer HisThrIleThr GluAspSerLys
529 -+---------+ ----------+-- -------+---- -----+------ 576
    CCAAGTCAAGAG GATGAGGTGATA ATCGGCGGTCAA GGTCAGGTGATT
    ProSerGlnGlu AspGluValIle IleGlyGlyGln GlyGlnValIle
577 ---+-------- -+---------+ ----------+-- -------+---- 624
    GACTTTACAGAA GATACTCAATCT GGTATGTCTGGG GATAATAGCCAT
    AspPheThrGlu AspThrGlnSer GlyMetSerGly AspAsnSerHis
625 -----+------ ---+-------- -+---------+ ----------+-- 672
    ACAGATGGGACA GTGCTTGAAGAA GACTCTAAACCA AGTCAAGAGGAT
    ThrAspGlyThr ValLeuGluGlu AspSerLysPro SerGlnGluAsp
673 --------+---- -----+------ ---+-------- -+---------+ 720
    GAGGTGATAATC GGCGGTCAAGGT CAAGTGATTGAC TTTACAGAAGAT
    GluValIleIle GlyGlyGlnGly GlnValIleAsp PheThrGluAsp
```

FIG. 4

```
 721 ----------+-- -------+---- -----+------ ---+--------  768
     ACCCAAACCGGT ATGTCTGGGGCT GGACAAGTAGAG AGTCCAACAATC
     ThrGlnThrGly MetSerGlyAla GlyGlnValGlu SerProThrIle
 769 -+---------+ ----------+-- --------+---- -----+------  816
     ACCGAAGAAACC CATAAACCAGAA ATAATCATGGGC GGTCAAAGTGAC
     ThrGluGluThr HisLysProGlu IleIleMetGly GlyGlnSerAsp
 817 ---+-------- -+---------+ ----------+-- --------+----  864
     CCTATTGATATG GTTGAGGACACT CTTCCTGGTATG TCTGGCTCTAAT
     ProIleAspMet ValGluAspThr LeuProGlyMet SerGlySerAsn
 865 -----+------ ---+-------- -+---------+ ----------+--   912
     GAAGCTACTGTT GTGGAAGAAGAC ACACGTCCTAAA CTTCAATTCCAT
     GluAlaThrVal ValGluGluAsp ThrArgProLys LeuGlnPheHis
 913 -------+---- -----+------ ---+-------- -+---------+   960
     TTTGATAATGAA GAGCCCGTTCCT GCAACGGTTCCA ACCGTTTCTCAA
     PheAspAsnGlu GluProValPro AlaThrValPro ThrValSerGln
 961 ---------+-- -------+---- -----+------ ---+--------  1008
     ACTCCTATTGCT CAGGTAGAAAGT AAAGTGCCTCAT GCCAAAGCAGAG
     ThrProIleAla GlnValGluSer LysValProHis AlaLysAlaGlu
1009 -+---------+ ----------+-- --------+---- -----+------ 1056
     AGTGCGTTACCT CAAACTGGAGAT ACAAATAAACTA GAAACGTTCTTT
     SerAlaLeuPro GlnThrGlyAsp ThrAsnLysLeu GluThrPhePhe
1057 ---+-------- -+---------+ ----------+-- --------+---- 1104
     ACCATTACAGCA CTAACTGTTATT GGAGCGGCAGGA TTACTAGGCAAA
     ThrIleThrAla LeuThrValIle GlyAlaAlaGly LeuLeuGlyLys
1105 -----+------ ---+-------- -+---------+ ----------+--  1152
     AAACGTCGTAAT AATCAAACTGAT TAATCAGCAGAT TTCATCAAACGC
     LysArgArgAsn AsnGlnThrAsp EndSerAlaAsp PheIleLysArg
1153 -------+---- -----+------ ---+-------- -+---------+  1200
     TATAAACAAGGC TAACATTTTAGC CTTGTTTTATAT TGTTTCACTGAC
     TyrLysGlnGly End
1201 ---------+-- -------+---- -----+------ ---+--------  1248
     CTCTAAAAGTTA TGACTGTTTTAA AGGGGGGGTAGG CCAATCCTCAAA
1249 -+---------+ ----------+-- --------+---- -----+------ 1296
     AGTAGTTAAGTT GAGAAACACCAC ATCACTTTAGTC TTACTGCGCATA
1297 ---+-------- -+---------+ ----------+-- --------+---- 1344
     CTAAAAGCAAAA GATAATTAGGAG CACTTGCTAACT GGAAAAAATCAA
1345 -----+------ ---+-------- -+----  1374
     ATGCAAAGCTAG TTGCCAAAGAAC TCTAGA
```

F I G. 5

```
1   ----------+--  --------+----  -----+------  ---+--------  48
    CTCGAGGAAACT  TTGCCAACAGAG  GAACATCAATCA  GGTGATACCACA
    LeuGluGluThr  LeuProThrGlu  GluHisGlnSer  GlyAspThrThr
49  -+---------+  ----------+--  --------+----  -----+------  96
    ACTATTGAAGAT  ACTCGCCCGATT  GATACCATGTCA  GGTCTATCAGGA
    ThrIleGluAsp  ThrArgProIle  AspThrMetSer  GlyLeuSerGly
97  ---+--------  -+---------+  ----------+--  --------+----  144
    GAGACTGGGCAG  TCTGGTAATACT  ACAATTGAGGAA  GATAGTACGACT
    GluThrGlyGln  SerGlyAsnThr  ThrIleGluGlu  AspSerThrThr
145 -----+------  ---+--------  -+---------+  ----------+--  192
    CACGTTAAATTC  TCAAAACGTGAT  ATTAATGGTAAA  GAACTAGCAGGT
    HisValLysPhe  SerLysArgAsp  IleAsnGlyLys  GluLeuAlaGly
193 ---------+--  -----+------  ---+--------  -+---------+  240
    GCTATGATTGAA  CTACGTAATCTA  TCAGGTCAAACT  ATTCAATCATGG
    AlaMetIleGlu  LeuArgAsnLeu  SerGlyGlnThr  IleGlnSerTrp
241 ----------+--  --------+----  -----+------  ---+--------  288
    ATATCAGACGGC  ACAGTTAAAGTT  TTCTACTTGATG  CCAGGGACTTAT
    IleSerAspGly  ThrValLysVal  PheTyrLeuMet  ProGlyThrTyr
289 -+---------+  ----------+--  --------+----  -----+------  336
    CAATTTGTGGAG  ACGGCAGCGCCA  GAAGGTTATGAA  TTGGCAGCTCCA
    GlnPheValGlu  ThrAlaAlaPro  GluGlyTyrGlu  LeuAlaAlaPro
337 ---+--------  -+---------+  ----------+--  --------+----  384
    ATTACCTTCACA  ATTGATGAGAAA  GGACAAATTTGG  GTAGACAGTACA
    IleThrPheThr  IleAspGluLys  GlyGlnIleTrp  ValAspSerThr
433 --------+----  -----+------  ---+--------  -+---------+  480
    ATTACTGAGGCG  AGTCAATCTATT  GATTTCGAGGAA  ACTTTACCAACT
    IleThrGluAla  SerGlnSerIle  AspPheGluGlu  ThrLeuProThr
481 ----------+--  --------+----  -----+------  ---+--------  528
    GAACAAGGCCAA  TCTGGCTCTACA  ACGGAGGTTGAG  GATACTAAAGGC
    GluGlnGlyGln  SerGlySerThr  ThrGluValGlu  AspThrLysGly
529 -+---------+  ----------+--  --------+----  -----+------  576
    CCAGAAGTCATT  ATCGGCGGTCAG  GGAGAGATTGTT  GATATCGAGGAG
    ProGluValIle  IleGlyGlyGln  GlyGluIleVal  AspIleGluGlu
577 ---+--------  -+---------+  ----------+--  --------+----  624
    AACTTACCAACT  GAACAAGGCCAA  TCTGGCTCTACA  ACTGAAGTAGAG
    AsnLeuProThr  GluGlnGlyGln  SerGlySerThr  ThrGluValGlu
625 -----+------  ---+--------  -+---------+  ----------+--  672
    GATACTAAAGGC  CCAGAAGTCATT  ATCGGCGGTCAA  GGAGAGGTTGTT
    AspThrLysGly  ProGluValIle  IleGlyGlyGln  GlyGluValVal
673 --------+----  -----+------  ---+--------  -+---------+  720
    GATATTGAGGAG  AGCTTACCAACT  GAACAAGGCCAA  TCTGGCTCTACA
    AspIleGluGlu  SerLeuProThr  GluGlnGlyGln  SerGlySerThr
721 ----------+--  --+----+----  -----+--------  ---+--------  768
    ACTGAAGTAGAA  GATAGCAAGCCT  AAACTCTCTATC  CACTTTGATAAC
    ThrGluValGlu  AspSerLysPro  LysLeuSerIle  HisPheAspAsn
```

FIG. 5

```
769 -+---------+ ----------+-- --------+---- -----+------ 816
    GAGTGGCCTAAG GAAGACAAACCA CAACTACCTGCC GTTGAAAAACCT
    GluTrpProLys GluAspLysPro GlnLeuProAla ValGluLysPro
817 ---+-------- -+---------+ ----------+-- -------+---- 864
    AAGACTAAGGAG AGCTTGCCAGCC GCAGGGGAAGCT GAACATGTCTTA
    LysThrLysGlu SerLeuProAla AlaGlyGluAls GluHisValLeu
865 -----+------ ---+-------- 888
    TCTACTATCGTG GGAGCAATGATC
    SerThrIleVal GlyAlaMetIle
```

5,866,541

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1371 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTAGATACCT  CAGAAAACAA  AAAATCTGTA  ACTGAAAAAG  TAATAACTAG  CGATGTTAAA        60
TATAAGATTA  ATGATAAAGA  AGTGAAAGGT  AAAGAACTAG  ACGATGTCTC  TTTAACTTAC       120
AGTAAAGAAA  CCGTTCGTAA  GCCACAGGTG  GAACCAAATG  TTCCTGATAC  ACCTCAGGAA       180
AAACCATTGA  CACCGCTTGC  ACCGTCAGAA  CCTTCACAAC  CATCTATTCC  AGAGACACCA       240
CTGATACCGT  CAGAACCTTC  AGTTCCAGAG  ACATCAACAC  CAGAAGGTCC  AACAGAGGGA       300
GAAAATAATC  TTGGTGGTCA  GAGTGAAATA  ACGATTACAG  AAGATTCTCA  ATCAGGGATG       360
TCTGGTCAAA  ATCCTGGTTC  TGGAAATGAA  ACAGTGGTTG  AAGACACTCA  AACAAGTCAA       420
GAGGATATTG  TACTTGGTGG  TCCAGGTCAA  GTGATTGACT  TTACAGAAGA  TAGCCAACCG       480
GGTATGTCTG  GTAATAATAG  CCATACTATT  ACAGAAGATT  CTAAACCAAG  TCAAGAGGAT       540
GAGGTGATAA  TCGGCGGTCA  AGGTCAGGTG  ATTGACTTTA  CAGAAGATAC  TCAATCTGGT       600
ATGTCTGGGG  ATAATAGCCA  TACAGATGGG  ACAGTGCTTG  AAGAAGACTC  TAAACCAAGT       660
CAAGAGGATG  AGGTGATAAT  CGGCGGTCAA  GGTCAACTGA  TTGACTTTAC  AGAAGATACC       720
CAAACCGGTA  TGTCTGGGGC  TGGACAAGTA  GAGAGTCCAA  CAACTACCGA  AGAAACCCAT       780
AAACCAGAAA  TAATCATGGG  CGGTCAAAGT  GACCCTATTG  ATATGGTTGA  GGACACTCTT       840
CCTGGTATGT  CTGGCTCTAA  TGAAGCTACT  GTTGTGGAAG  AAGACACACG  TCCTAAACTT       900
CAATTCCATT  TTGATAATGA  AGAGCCCGTT  CCTGCAACGG  TTCCAACCGT  TTCTCAAACT       960
CCTATTGCTC  AGGTAGAAAG  TAAAGTGCCT  CATGCCAAAG  CAGAGAGTGC  GTTACCTCAA      1020
ACTGGAGATA  CAAATAAACT  AGAAACGTTC  TTTACCATTA  CAGCACTAAC  TGTTATTGGA      1080
GCGGCAGGAT  TACTAGGCAA  AAAACGTCGT  AATAATCAAA  CTGATTTATC  AGCAGATTTC      1140
ATCAAACGCT  ATAAACAAGG  CTAACATTTT  AGCCTTGTTT  TATATTGTTT  CACTGACCTC      1200
TAAAGTTAT   GACTGTTTTA  AAGGGGGGT   AGGCCAATCC  TCAAAGTAG   TTAAGTTGAG      1260
AAACACCACA  TCACTTTAGT  CTTACTGCGC  ATACTAAAAG  CAAAAGATAA  TTAGGAGCAG      1320
TTGCTAACTG  GAAAAAATCA  AATGCAAAGC  TAGTTGCCAA  AGAACTCTAG  A                1371
```

( 2 ) INFORMATION FOR SEQ ID NO:2:

( i ) SEQUENCE CHARACTERISTICS:
        ( A ) LENGTH: 840 base pairs ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| CTCGAGGAAA | CTTTGCCAAA | CGAGGAACAT | CAATCAGGTG | ATACCACAAC | TATTGAAGAT | 60 |
| ACTCGCCCGA | TTGATACCAT | GTCAGGTCTA | TCAGGAGAGA | CTGGGCAGTC | TGGTAATACT | 120 |
| ACAATTGAGG | AAGATAGTAC | GACTCACGTT | AAATTCTCAA | AACGTGATAT | TAATGGTAAA | 180 |
| GAACTAGCAG | GTGCTATGAT | TGAACTACGT | AATCTATCAG | GTCAAACTAT | TCAATCATGG | 240 |
| ATATCAGACG | GCACAGTTAA | AGTTTTCTAC | TTGATGCCAG | GGACTTATCA | ATTTGTGGAG | 300 |
| ACGGCAGCGC | CAGAAGGTTA | TGAATTGGCA | GCTCCAATTA | CCTTCACAAT | TGATGAGAAA | 360 |
| GGACAAATTT | GGGTAGACAG | TACAATTACT | GAGGCGAGTC | AATCTATTGA | TTTCGAGGAA | 420 |
| ACTTTACCAA | CTGAACAAGG | CCAATCTGGC | TCTACAACGG | AGGTTGAGGA | TACTAAAGGC | 480 |
| CCAGAAGTCA | TTATCGGCGG | TCAGGGAGAG | ATTGTTGATA | TCGAGGAGAA | CTTACCAACT | 540 |
| GAACAAGGCC | AATCTGGCTC | TACAACTGAA | GTAGAGGATA | CTAAAGGCCC | AGAAGTCATT | 600 |
| ATCGGCGGTC | AAGGAGAGGT | TGTTGATATT | GAGGAGAGCT | TACCAACTGA | ACAAGGCCAA | 660 |
| TCTGGCTCTA | CAACTGAAGT | AGAAGATAGC | AAGCCTAAAC | TCTCTATCCA | CTTTGATAAC | 720 |
| GAGTGGCCTA | AGGAAGACAA | ACCACAACTA | CCTGCCGTTG | AAAAACCTAA | GACTAAGGAG | 780 |
| AGCTTGCCAG | CCGCAGGGGA | AGCTGAACAT | GTCTTATCTA | CTATCGTGGG | AGCAATGATC | 840 |

( 2 ) INFORMATION FOR SEQ ID NO:3:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| GAAGACACTC | AAACAAGTCA | AGAGGATATT | GTACTTGGTG | GTCCAGGTCA | AGTGATTGAC | 60 |
| TTTACAGAAG | ATAGCCAACC | GGGTATGTCT | GGTAATAATA | GCCATACTAT | TACAGAAGAT | 120 |
| TCTAAACCAA | GTCAAGAGGA | TGAGGTGATA | ATCGGCGGTC | AAGGTCAGGT | GATTGACTTT | 180 |
| ACAGAAGATA | CTCAATCTGG | TATGTCTGGG | GATAATAGCC | ATACAGATGG | GACAGTGCTT | 240 |
| GAAGAAGACT | CTAAACCAAG | TCAAGAGGAT | GAGGTGATAA | TCGGCGGTCA | AGGTCAACTG | 300 |
| ATTGACTTTA | CAGAAGATAC | CCAAACCGGT | ATGTCTGGG | | | 339 |

( 2 ) INFORMATION FOR SEQ ID NO:4:

( i ) SEQUENCE CHARACTERISTICS:
        ( A ) LENGTH: 273 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| GAGGAAACTT | TACCAACTGA | ACAAGGCCAA | TCTGGCTCTA | CAACGGAGGT | TGAGGATACT | 60 |
| AAAGGCCCAG | AAGTCATTAT | CGGCGGTCAG | GGAGAGATTG | TTGATATCGA | GGAGAACTTA | 120 |
| CCAACTGAAC | AAGGCCAATC | TGGCTCTACA | ACTGAAGTAG | AGGATACTAA | AGGCCCAGAA | 180 |

```
GTCATTATCG GCGGTCAAGG AGAGGTTGTT GATATTGAGG AGAGCTTACC AACTGAACAA          240

GGCCAATCTG GCTCTACAAC TGAAGTAGAA GAT                                       273
```

( 2 ) INFORMATION FOR SEQ ID NO:5:

( i ) SEQUENCE CHARACTERISTICS:
        ( A ) LENGTH: 112 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Glu Asp Thr Gln Thr Ser Gln Glu Asp Ile Val Leu Gly Gly Pro Gly
 1               5                  10                  15

Gln Val Ile Asp Phe Thr Glu Asp Ser Gln Pro Gly Met Ser Gly Asn
            20                  25                  30

Ser His Thr Ile Thr Glu Asp Lys Pro Ser Gln Glu Asp Glu Val
        35                  40                  45

Ile Ile Gly Gly Gln Gly Gln Val Ile Asp Phe Thr Glu Asp Thr Gln
        50                  55                  60

Ser Gly Met Ser Gly Asp Asn Ser His Thr Asp Gly Thr Val Leu Glu
65                  70                  75                  80

Glu Asp Ser Lys Pro Ser Gln Glu Asp Glu Val Ile Ile Gly Gly Gln
                85                  90                  95

Gly Gln Val Ile Asp Phe Thr Glu Asp Thr Gln Thr Gly Met Ser Gly
                100                 105                 110
```

( 2 ) INFORMATION FOR SEQ ID NO:6:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Glu Glu Thr Leu Pro Thr Glu Gln Gly Gln Ser Gly Ser Thr Thr Glu
 1               5                  10                  15

Val Glu Asp Thr Lys Gly Pro Glu Val Ile Ile Gly Gly Gln Gly Glu
            20                  25                  30

Ile Val Asp Ile Glu Glu Asn Leu Pro Thr Glu Gln Gly Gln Ser Gly
        35                  40                  45

Ser Thr Thr Glu Val Glu Asp Thr Lys Gly Pro Glu Val Ile Ile Gly
        50                  55                  60

Gly Gln Gly Glu Val Val Asp Ile Glu Glu Ser Leu Pro Thr Glu Gln
65                  70                  75                  80

Gly Gln Ser Gly Gly Ser Thr Thr Glu Val Glu Asp
                85                  90
```

( 2 ) INFORMATION FOR SEQ ID NO:7:

( i ) SEQUENCE CHARACTERISTICS:
        ( A ) LENGTH: 158 amino acids
        ( B ) TYPE: amino acid
        ( C ) STRANDEDNESS: single
        ( D ) TOPOLOGY: linear ( i i ) MOLECULE TYPE: protein (x i) SEQUENCE DESCRIPTION: SEQ ID NO:7:

| Glu | Asp | Thr | Gln | Thr | Ser | Gln | Glu | Asp | Ile | Val | Leu | Gly | Gly | Pro | Gly |
| 1 | | | | 5 | | | | | 10 | | | | | 15 | |

| Gln | Val | Ile | Asp | Phe | Thr | Glu | Asp | Ser | Gln | Pro | Gly | Met | Ser | Gly | Asn |
| | | | 20 | | | | | 25 | | | | | 30 | | |

| Asn | Ser | His | Thr | Thr | Glu | Asp | Ser | Lys | Pro | Ser | Gln | Glu | Asp | Glu | Val |
| | | 35 | | | | | 40 | | | | | 45 | | | |

| Ile | Ile | Gly | Gly | Gln | Gly | Gln | Val | Ile | Asp | Phe | Thr | Glu | Asp | Thr | Gln |
| | 50 | | | | | 55 | | | | | 60 | | | | |

| Ser | Gly | Met | Ser | Gly | Asp | Asn | Ser | His | Thr | Asp | Gly | Thr | Val | Leu | Glu |
| 65 | | | | | 70 | | | | | 75 | | | | | 80 |

| Glu | Asp | Ser | Lys | Pro | Ser | Gln | Glu | Asp | Glu | Val | Ile | Ile | Gly | Gly | Gln |
| | | | | 85 | | | | | 90 | | | | | 95 | |

| Gly | Gln | Val | Ile | Asp | Phe | Thr | Glu | Asp | Thr | Gln | Thr | Gly | Met | Ser | Gly |
| | | | 100 | | | | | 105 | | | | | 110 | | |

| Ala | Gly | Gln | Val | Glu | Ser | Pro | Thr | Ile | Thr | Glu | Glu | Thr | His | Lys | Pro |
| | | 115 | | | | | 120 | | | | | 125 | | | |

| Glu | Ile | Ile | Met | Gly | Gly | Gln | Ser | Asp | Pro | Ile | Asp | Met | Val | Glu | Asp |
| | 130 | | | | | 135 | | | | | 140 | | | | |

| Thr | Leu | Pro | Gly | Met | Ser | Gly | Ser | Asn | Glu | Ala | Glu | Asp | Thr |
| 145 | | | | | 150 | | | | | 155 | | | |

(2) INFORMATION FOR SEQ ID NO:8:

(i) SEQUENCE CHARACTERISTICS:
  (A) LENGTH: 108 amino acids
  (B) TYPE: amino acid
  (C) STRANDEDNESS: single
  (D) TOPOLOGY: linear (i i) MOLECULE TYPE: protein (x i) SEQUENCE DESCRIPTION: SEQ ID NO:8:

| Glu | Glu | Thr | Leu | Pro | Thr | Glu | Gln | Gly | Gln | Ser | Gly | Ser | Thr | Thr | Glu |
| 1 | | | | 5 | | | | | 10 | | | | | 15 | |

| Val | Glu | Asp | Thr | Lys | Gly | Pro | Glu | Val | Ile | Ile | Gly | Gly | Gln | Gly | Glu |
| | | | 20 | | | | | 25 | | | | | 30 | | |

| Ile | Val | Asp | Ile | Glu | Glu | Asn | Leu | Pro | Thr | Glu | Gln | Gly | Gln | Ser | Gly |
| | | | 35 | | | | | 40 | | | | | 45 | | |

| Ser | Thr | Thr | Glu | Val | Glu | Asp | Thr | Lys | Gly | Pro | Glu | Val | Ile | Ile | Gly |
| | | 50 | | | | | 55 | | | | | 60 | | | |

| Gly | Gln | Gly | Glu | Val | Val | Asp | Ile | Glu | Glu | Ser | Leu | Pro | Thr | Glu | Gln |
| 65 | | | | | 70 | | | | | 75 | | | | | 80 |

| Gly | Gln | Ser | Gly | Ser | Thr | Thr | Glu | Val | Glu | Asp | Ser | Lys | Pro | Lys | Leu |
| | | | | 85 | | | | | 90 | | | | | 95 | |

| Ser | Ile | His | Phe | Asp | Asn | Glu | Trp | Pro | Lys | Glu | Asp |
| | | | 100 | | | | | 105 | | | |

(2) INFORMATION FOR SEQ ID NO:9:

(i) SEQUENCE CHARACTERISTICS:
  (A) LENGTH: 1374 base pairs
  (B) TYPE: nucleic acid
  (C) STRANDEDNESS: single
  (D) TOPOLOGY: linear (i i) MOLECULE TYPE: DNA (genomic)

(i x) FEATURE:
  (A) NAME/KEY: CDS
  (B) LOCATION: 1..1164

( x i ) SEQUENCE DESCRIPTION: SEQ ID NO:9:

| | | | | | | | | | | | | | | | | |
|---|---|---|---|---|---|---|---|---|---|---|---|---|---|---|---|---|
| CTA | GAT | ACC | TCA | GAA | AAC | AAA | AAA | TCT | GTA | ACT | GAA | AAA | GTA | ATA | ACT | 48 |
| Leu | Asp | Thr | Ser | Glu | Asn | Lys | Lys | Ser | Val | Thr | Glu | Lys | Val | Ile | Thr | |
| 1 | | | | 5 | | | | | 10 | | | | | 15 | | |
| AGC | GAT | GTT | AAA | TAT | AAG | ATT | AAT | GAT | AAA | GAA | GTG | AAA | GGT | AAA | GAA | 96 |
| Ser | Asp | Val | Lys | Tyr | Lys | Ile | Asn | Asp | Lys | Glu | Val | Lys | Gly | Lys | Glu | |
| | | | 20 | | | | | 25 | | | | | 30 | | | |
| CTA | GAC | GAT | GTC | TCT | TTA | ACT | TAC | AGT | AAA | GAA | ACC | GTT | CGT | AAG | CCA | 144 |
| Leu | Asp | Asp | Val | Ser | Leu | Thr | Tyr | Ser | Lys | Glu | Thr | Val | Arg | Lys | Pro | |
| | | 35 | | | | | 40 | | | | | 45 | | | | |
| CAG | GTG | GAA | CCA | AAT | GTT | CCT | GAT | ACA | CCT | CAG | GAA | AAA | CCA | TTG | ACA | 192 |
| Gln | Val | Glu | Pro | Asn | Val | Pro | Asp | Thr | Pro | Gln | Glu | Lys | Pro | Leu | Thr | |
| | 50 | | | | | 55 | | | | | 60 | | | | | |
| CCG | CTT | GCA | CCG | TCA | GAA | CCT | TCA | CAA | CCA | TCT | ATT | CCA | GAG | ACA | CCA | 240 |
| Pro | Leu | Ala | Pro | Ser | Glu | Pro | Ser | Gln | Pro | Ser | Ile | Pro | Glu | Thr | Pro | |
| 65 | | | | | 70 | | | | | 75 | | | | | 80 | |
| CTG | ATA | CCG | TCA | GAA | CCT | TCA | GTT | CCA | GAG | ACA | TCA | ACA | CCA | GAA | GGT | 288 |
| Leu | Ile | Pro | Ser | Glu | Pro | Ser | Val | Pro | Glu | Thr | Ser | Thr | Pro | Glu | Gly | |
| | | | | 85 | | | | | 90 | | | | | 95 | | |
| CCA | ACA | GAG | GGA | GAA | AAT | AAT | CTT | GGT | GGT | CAG | AGT | GAA | GAG | ATA | ACG | 336 |
| Pro | Thr | Glu | Gly | Glu | Asn | Asn | Leu | Gly | Gly | Gln | Ser | Glu | Glu | Ile | Thr | |
| | | | 100 | | | | | 105 | | | | | 110 | | | |
| ATT | ACA | GAA | GAT | TCT | CAA | TCA | GGG | ATG | TCT | GGT | CAA | AAT | CCT | GGT | TCT | 384 |
| Ile | Thr | Glu | Asp | Ser | Gln | Ser | Gly | Met | Ser | Gly | Gln | Asn | Pro | Gly | Ser | |
| | | 115 | | | | | 120 | | | | | 125 | | | | |
| GGA | AAT | GAA | ACA | GTG | GTT | GAA | GAC | ACT | CAA | ACA | AGT | CAA | GAG | GAT | ATT | 432 |
| Gly | Asn | Glu | Thr | Val | Val | Glu | Asp | Thr | Gln | Thr | Ser | Gln | Glu | Asp | Ile | |
| | 130 | | | | | 135 | | | | | 140 | | | | | |
| GTA | CTT | GGT | GGT | CCA | GGT | CAA | GTG | ATT | GAC | TTT | ACA | GAA | GAT | AGC | CAA | 480 |
| Val | Leu | Gly | Gly | Pro | Gly | Gln | Val | Ile | Asp | Phe | Thr | Glu | Asp | Ser | Gln | |
| 145 | | | | | 150 | | | | | 155 | | | | | 160 | |
| CCG | GGT | ATG | TCT | GGT | AAT | AAT | AGC | CAT | ACT | ATT | ACA | GAA | GAT | TCT | AAA | 528 |
| Pro | Gly | Met | Ser | Gly | Asn | Asn | Ser | His | Thr | Ile | Thr | Glu | Asp | Ser | Lys | |
| | | | | 165 | | | | | 170 | | | | | 175 | | |
| CCA | AGT | CAA | GAG | GAT | GAG | GTG | ATA | ATC | GGC | GGT | CAA | GGT | CAG | GTG | ATT | 576 |
| Pro | Ser | Gln | Glu | Asp | Glu | Val | Ile | Ile | Gly | Gly | Gln | Gly | Gln | Val | Ile | |
| | | | 180 | | | | | 185 | | | | | 190 | | | |
| GAC | TTT | ACA | GAA | GAT | ACT | CAA | TCT | GGT | ATG | TCT | GGG | GAT | AAT | AGC | CAT | 624 |
| Asp | Phe | Thr | Glu | Asp | Thr | Gln | Ser | Gly | Met | Ser | Gly | Asp | Asn | Ser | His | |
| | | 195 | | | | | 200 | | | | | 205 | | | | |
| ACA | GAT | GGG | ACA | GTG | CTT | GAA | GAA | GAC | TCT | AAA | CCA | AGT | CAA | GAG | GAT | 672 |
| Thr | Asp | Gly | Thr | Val | Leu | Glu | Glu | Asp | Ser | Lys | Pro | Ser | Gln | Glu | Asp | |
| | 210 | | | | | 215 | | | | | 220 | | | | | |
| GAG | GTG | ATA | ATC | GGC | GGT | CAA | GGT | CAA | GTG | ATT | GAC | TTT | ACA | GAA | GAT | 720 |
| Glu | Val | Ile | Ile | Gly | Gly | Gln | Gly | Gln | Val | Ile | Asp | Phe | Thr | Glu | Asp | |
| 225 | | | | | 230 | | | | | 235 | | | | | 240 | |
| ACC | CAA | ACC | GGT | ATG | TCT | GGG | GCT | GGA | CAA | GTA | GAG | AGT | CCA | ACA | ATC | 768 |
| Thr | Gln | Thr | Gly | Met | Ser | Gly | Ala | Gly | Gln | Val | Glu | Ser | Pro | Thr | Ile | |
| | | | | 245 | | | | | 250 | | | | | 255 | | |
| ACC | GAA | GAA | ACC | CAT | AAA | CCA | GAA | ATA | ATC | ATG | GGC | GGT | CAA | AGT | GAC | 816 |
| Thr | Glu | Glu | Thr | His | Lys | Pro | Glu | Ile | Ile | Met | Gly | Gly | Gln | Ser | Asp | |
| | | | 260 | | | | | 265 | | | | | 270 | | | |
| CCT | ATT | GAT | ATG | GTT | GAG | GAC | ACT | CTT | CCT | GGT | ATG | TCT | GGC | TCT | AAT | 864 |
| Pro | Ile | Asp | Met | Val | Glu | Asp | Thr | Leu | Pro | Gly | Met | Ser | Gly | Ser | Asn | |
| | | 275 | | | | | 280 | | | | | 285 | | | | |
| GAA | GCT | ACT | GTT | GTG | GAA | GAA | GAC | ACA | CGT | CCT | AAA | CTT | CAA | TTC | CAT | 912 |
| Glu | Ala | Thr | Val | Val | Glu | Glu | Asp | Thr | Arg | Pro | Lys | Leu | Gln | Phe | His | |
| | 290 | | | | | 295 | | | | | 300 | | | | | |

```
TTT  GAT  AAT  GAA  GAG  CCC  GTT  CCT  GCA  ACG  GTT  CCA  ACC  GTT  TCT  CAA         960
Phe  Asp  Asn  Glu  Glu  Pro  Val  Pro  Ala  Thr  Val  Pro  Thr  Val  Ser  Gln
305                 310                      315                      320

ACT  CCT  ATT  GCT  CAG  GTA  GAA  AGT  AAA  GTG  CCT  CAT  GCC  AAA  GCA  GAG        1008
Thr  Pro  Ile  Ala  Gln  Val  Glu  Ser  Lys  Val  Pro  His  Ala  Lys  Ala  Glu
                    325                      330                      335

AGT  GCG  TTA  CCT  CAA  ACT  GGA  GAT  ACA  AAT  AAA  CTA  GAA  ACG  TTC  TTT        1056
Ser  Ala  Leu  Pro  Gln  Thr  Gly  Asp  Thr  Asn  Lys  Leu  Glu  Thr  Phe  Phe
               340                      345                      350

ACC  ATT  ACA  GCA  CTA  ACT  GTT  ATT  GGA  GCG  GCA  GGA  TTA  CTA  GGC  AAA        1104
Thr  Ile  Thr  Ala  Leu  Thr  Val  Ile  Gly  Ala  Ala  Gly  Leu  Leu  Gly  Lys
          355                      360                      365

AAA  CGT  CGT  AAT  AAT  CAA  ACT  GAT  TAA  TCA  GCA  GAT  TTC  ATC  AAA  CGC        1152
Lys  Arg  Arg  Asn  Asn  Gln  Thr  Asp  *    Ser  Ala  Asp  Phe  Ile  Lys  Arg
     370                      375                      380

TAT  AAA  CAA  GGC  TAACATTTTA  GCCTTGTTTT  ATATTGTTTC  ACTGACCTCT                    1204
Tyr  Lys  Gln  Gly
385

AAAAGTTATG  ACTGTTTTAA  AGGGGGGGTA  GGCCAATCCT  CAAAAGTAGT  TAAGTTGAGA                 1264

AACACCACAT  CACTTTAGTC  TTACTGCGCA  TACTAAAAGC  AAAAGATAAT  TAGGAGCAGT                 1324

TGCTAACTGG  AAAAAATCAA  ATGCAAAGCT  AGTTGCCAAA  GAACTCTAGA                             1374
```

( 2 ) INFORMATION FOR SEQ ID NO:10:

( i ) SEQUENCE CHARACTERISTICS:
        ( A ) LENGTH: 840 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 1..840

( x i ) SEQUENCE DESCRIPTION: SEQ ID NO:10:

```
CTC  GAG  GAA  ACT  TTG  CCA  ACA  GAG  GAA  CAT  CAA  TCA  GGT  GAT  ACC  ACA          48
Leu  Glu  Glu  Thr  Leu  Pro  Thr  Glu  Glu  His  Gln  Ser  Gly  Asp  Thr  Thr
     390                      395                      400

ACT  ATT  GAA  GAT  ACT  CGC  CCG  ATT  GAT  ACC  ATG  TCA  GGT  CTA  TCA  GGA          96
Thr  Ile  Glu  Asp  Thr  Arg  Pro  Ile  Asp  Thr  Met  Ser  Gly  Leu  Ser  Gly
405                      410                      415                      420

GAG  ACT  GGG  CAG  TCT  GGT  AAT  ACT  ACA  ATT  GAG  GAA  GAT  AGT  ACG  ACT         144
Glu  Thr  Gly  Gln  Ser  Gly  Asn  Thr  Thr  Ile  Glu  Glu  Asp  Ser  Thr  Thr
                    425                      430                      435

CAC  GTT  AAA  TTC  TCA  AAA  CGT  GAT  ATT  AAT  GGT  AAA  GAA  CTA  GCA  GGT         192
His  Val  Lys  Phe  Ser  Lys  Arg  Asp  Ile  Asn  Gly  Lys  Glu  Leu  Ala  Gly
               440                      445                      450

GCT  ATG  ATT  GAA  CTA  CGT  AAT  CTA  TCA  GGT  CAA  ACT  ATT  CAA  TCA  TGG         240
Ala  Met  Ile  Glu  Leu  Arg  Asn  Leu  Ser  Gly  Gln  Thr  Ile  Gln  Ser  Trp
          455                      460                      465

ATA  TCA  GAC  GGC  ACA  GTT  AAA  GTT  TTC  TAC  TTG  ATG  CCA  GGG  ACT  TAT         288
Ile  Ser  Asp  Gly  Thr  Val  Lys  Val  Phe  Tyr  Leu  Met  Pro  Gly  Thr  Tyr
     470                      475                      480

CAA  TTT  GTG  GAG  ACG  GCA  GCG  CCA  GAA  GGT  TAT  GAA  TTG  GCA  GCT  CCA         336
Gln  Phe  Val  Glu  Thr  Ala  Ala  Pro  Glu  Gly  Tyr  Glu  Leu  Ala  Ala  Pro
485                      490                      495                      500

ATT  ACC  TTC  ACA  ATT  GAT  GAG  AAA  GGA  CAA  ATT  TGG  GTA  GAC  AGT  ACA         384
Ile  Thr  Phe  Thr  Ile  Asp  Glu  Lys  Gly  Gln  Ile  Trp  Val  Asp  Ser  Thr
                    505                      510                      515
```

-continued

```
ATT  ACT  GAG  GCG  AGT  CAA  TCT  ATT  GAT  TTC  GAG  GAA  ACT  TTA  CCA  ACT        432
Ile  Thr  Glu  Ala  Ser  Gln  Ser  Ile  Asp  Phe  Glu  Glu  Thr  Leu  Pro  Thr
               520                      525                      530

GAA  CAA  GGC  CAA  TCT  GGC  TCT  ACA  ACG  GAG  GTT  GAG  GAT  ACT  AAA  GGC        480
Glu  Gln  Gly  Gln  Ser  Gly  Ser  Thr  Thr  Glu  Val  Glu  Asp  Thr  Lys  Gly
               535                      540                      545

CCA  GAA  GTC  ATT  ATC  GGC  GGT  CAG  GGA  GAG  ATT  GTT  GAT  ATC  GAG  GAG        528
Pro  Glu  Val  Ile  Ile  Gly  Gly  Gln  Gly  Glu  Ile  Val  Asp  Ile  Glu  Glu
     550                      555                      560

AAC  TTA  CCA  ACT  GAA  CAA  GGC  CAA  TCT  GGC  TCT  ACA  ACT  GAA  GTA  GAG        576
Asn  Leu  Pro  Thr  Glu  Gln  Gly  Gln  Ser  Gly  Ser  Thr  Thr  Glu  Val  Glu
565                      570                      575                      580

GAT  ACT  AAA  GGC  CCA  GAA  GTC  ATT  ATC  GGC  GGT  CAA  GGA  GAG  GTT  GTT        624
Asp  Thr  Lys  Gly  Pro  Glu  Val  Ile  Ile  Gly  Gly  Gln  Gly  Glu  Val  Val
                    585                      590                      595

GAT  ATT  GAG  GAG  AGC  TTA  CCA  ACT  GAA  CAA  GGC  CAA  TCT  GGC  TCT  ACA        672
Asp  Ile  Glu  Glu  Ser  Leu  Pro  Thr  Glu  Gln  Gly  Gln  Ser  Gly  Ser  Thr
               600                      605                      610

ACT  GAA  GTA  GAA  GAT  AGC  AAG  CCT  AAA  CTC  TCT  ATC  CAC  TTT  GAT  AAC        720
Thr  Glu  Val  Glu  Asp  Ser  Lys  Pro  Lys  Leu  Ser  Ile  His  Phe  Asp  Asn
          615                      620                      625

GAG  TGG  CCT  AAG  GAA  GAC  AAA  CCA  CAA  CTA  CCT  GCC  GTT  GAA  AAA  CCT        768
Glu  Trp  Pro  Lys  Glu  Asp  Lys  Pro  Gln  Leu  Pro  Ala  Val  Glu  Lys  Pro
     630                      635                      640

AAG  ACT  AAG  GAG  AGC  TTG  CCA  GCC  GCA  GGG  GAA  GCT  GAA  CAT  GTC  TTA        816
Lys  Thr  Lys  Glu  Ser  Leu  Pro  Ala  Ala  Gly  Glu  Ala  Glu  His  Val  Leu
645                      650                      655                      660

TCT  ACT  ATC  GTG  GGA  GCA  ATG  ATC                                                 840
Ser  Thr  Ile  Val  Gly  Ala  Met  Ile
                    665
```

FIBRONECTION BINDING PROTEIN FROM *STREPTOCOCCUS DYSGALACTIAE*

This application is a divisional of application Ser. No. 08/125,222, filed Sep. 23, 1993; now U.S. Pat. No. 5,416,021, which is a continuation of Ser. No. 07/973,551, filed Nov. 9, 1992; now abandoned which is a continuation of Ser. No. 07/352,949, filed May 17, 1989, now abandoned.

TECHNICAL FIELD

The present invention relates to fibronectin binding proteins and hybrid-DNA molecules, e.g., plasmids or phages containing at least one nucleotide sequence encoding for said proteins. Further the invention relates to micro-organisms containing such molecules and their use to produce said proteins, and the synthetic production of said proteins.

The object of the present invention is to obtain minimal fibronectin binding proteins.

A further object of the present invention is to obtain said proteins by means of genetic engineering techniques using e.g., a plasmid containing a nucleotide sequence encoding for the proteins.

A further object of the present invention is to obtain a possibility to prepare said proteins by means of chemical synthesis.

BACKGROUND OF THE INVENTION

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen and/or laminin. It is further shown that fibronectin binding protein from *Staphylococcus aureus* has a molecular weight of 165 kD, and/or 87 kD, whereby it is probable that the smaller protein is a part of the larger one.

Fibronectin is a Large glycoprotein having a molecular weight of about 450 kD and having two similar subunits, which can have varying molecular sizes depending on a complex splicing pattern of the precursor mRNA. The protein is present in basement membranes, and connective tissue, but also in a soluble form in different body fluids, such as blood plasma (1). After the original discovery by Kuusela in 1978 that *S. aureus* binds to fibronectin (2) it has been shown that certain strains of other pathogenic bacteria, such as streptococci of different serological types (3), *E. coli* (4) and Salmonella (5) can bind to this protein (6).

Adhesion of pathogenic bacteria to surfaces is today a generally recognized concept in the discussions of wound pathogens using surface receptors to bind to different proteins on epithelium cell surfaces, in connective tissue matrix, and in wound crusts, such as e.g., fibronectin, fibrinogen, collagen and laminin. The problem is that these receptors are present in a relatively small amount on the bacterial cell surface, and that they are difficult to release. One feasible way in cases where the receptors consist of proteins is to clone the genes for the receptors in question to be able to prepare them in quantities which makes it considerably easier to study infections and the course of infections as well as prophylactic and therapeutic treatment of infections by wound pathogens.

Screening studies of different serological groups of streptococci, such as A, C, and G according to Lancefield (3) have shown that the strains tested can bind to different connective tissue proteins such as fibronectin, fibrinogen, collagen and laminin and different immunoglobulins (7,8) to a varying degree and with different specificity.

In order to further characterize fibronectin binding proteins from streptococci, particularly genes from *Streptococcus dysgalactiae* for such proteins have been cloned in *E. coli*. The fibronectin binding domains of these proteins have also been localized and properties and functions of proteins containing these domains will be discussed below.

DESCRIPTION OF THE PRESENT INVENTION

It has now surprisingly been shown possible to obtain hybrid-DNA molecules comprising nucleotide sequences of the genes coding for proteins or polypeptides having fibronectin binding properties. As evident from below the following nucleotide sequences [SEQ ID NOS:1 and 2] are present in the plasmids, pSDF102, and pSDF203, respectively, which encode said proteins.

CTA GAT ACC TCA GAA AAC AAA AAA TCT GTA ACT GAA AAA GTA ATA ACT AGC GAT GTT AAA TAT AAG ATT AAT GAT AAA GAA GTG AAA GGT AAA GAA CTA GAC GAT GTC TCT TTA ACT TAC AGT AAA GAA ACC GTT CGT AAG CCA CAG GTG GAA CCA AAT GTT CCT GAT ACA CCT CAG GAA AAA CCA TTG ACA CCG CTT GCA CCG TCA GAA CCT TCA CAA CCA TCT ATT CCA GAG ACA CCA CTG ATA CCG TCA GAA CCT TCA GTT CCA GAG ACA TCA ACA CCA GAA GGT CCA ACA GAG GGA GAA AAT AAT CTT GGT GGT CAG AGT GAA ATA ACG ATT ACA GAA GAT TCT CAA TCA GGG ATG TCT GGT CAA AAT CCT GGT TCT GGA AAT GAA ACA GTG GTT

GAA GAC ACT CAA ACA AGT CAA GAG GAT ATT GTA CTT GGT GGT CCA GGT CAA GTG ATT GAC TTT ACA GAA GAT AGC CAA CCG GGT ATG TCT GGT AAT AAT AGC CAT ACT ATT ACA

GAA GAT TCT AAA CCA AGT CAA GAG GAT GAG GTG ATA ATC GGC GGT CAA GGT CAG GTG ATT GAC TTT ACA GAA GAT ACT CAA TCT GGT ATG TCT GGG GAT AAT AGC CAT ACA GAT GGG ACA GTG CTT GAA

GAA GAC TCT AAA CCA AGT CAA GAG GAT GAG GTG ATA ATC GGC GGT CAA GGT CAA GTG ATT GAC TTT ACA GAA GAT ACC AAA ACC GGT ATG TCT GGG

GCT GGA CAA GTA GAG AGT CCA ACA ACT ACC GAA GAA ACC CAT AAA CCA GAA ATA ATC ATG GGC GGT CAA AGT GAC CCT ATT GAT ATG GTT GAG GAC ACT CTT CCT GGT ATG TCT GGC TCT AAT GAA GCT ACT GTT GTG GAA GAA GAC ACA CGT CCT AAA CTT CAA TTC CAT TTT GAT AAT GAA GAG CCC GTT CCT GCA ACG GTT CCA ACC GTT TCT CAA ACT CCT ATT GCT CAG GTA GAA AGT AAA GTG CCT CAT GCC AAA GCA GAG AGT GCG TTA CCT CAA ACT GGA GAT ACA AAT AAA CTA GAA ACG TTC TTT ACC ATT ACA GCA CTA ACT GTT ATT GGA GCG GCA GGA TTA CTA GGC AAA AAA CGT CGT AAT AAT CAA ACT GAT TAA TCA GCA GAT TTC ATC AAA CGC TAT AAA CAA GGC TAA CAT TTT AGC CTT GTT TTA TAT TGT TTC ACT GAC CTC TAA AAG TTA TGA CTG TTT TAA AGG GGG GGT AGG CCA ATC CTC AAA AGT AGT TAA GTT GAG AAA CAC CAC ATC ACT TTA GTC TTA CTG CGC ATA CTA AAA GCA AAA GAT AAT TAG GAG CAG TTG CTA ACT GGA AAA AAT CAA ATG CAA AGC TAG TTG CCA AAG AAC TCT AGA and/or

CTC GAG GAA ACT TTG CCA AAC GAG GAA CAT CAA TCA GGT GAT ACC ACA ACT ATT GAA GAT

ACT CGC CCG ATT GAT ACC ATG TCA GGT CTA
TCA GGA GAG ACT GGG CAG TCT GGT AAT ACT
ACA ATT GAG GAA GAT AGT ACG ACT CAC GTT
AAA TTC TCA AAA CGT GAT ATT AAT GGT AAA
GAA CTA GCA GGT GCT ATG ATT GAA CTA CGT
AAT CTA TCA GGT CAA ACT ATT CAA TCA TGG
ATA TCA GAC GGC ACA GTT AAA GTT TTC TAC
TTG ATG CCA GGG ACT TAT CAA TTT GTG GAG
ACG GCA GCG CCA GAA GGT TAT GAA TTG GCA
GCT CCA ATT ACC TTC ACA ATT GAT GAG AAA
GGA CAA ATT TGG GTA GAC AGT ACA ATT ACT
GAG GCG AGT CAA TCT ATT GAT TTC

GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC

GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT

GAG GAG AGC TTA CCA ACT GAA CAA GGC CAA
TCT GGC TCT ACA ACT GAA GTA GAA GAT

AGC AAG CCT AAA CTC TCT ATC CAC TTT GAT AAC
GAG TGG CCT AAG GAA GAC AAA CCA CAA CTA
CCT GCC GTT GAA AAA CCT AAG ACT AAG GAG
AGC TTG CCA GCC GCA GGG GAA GCT GAA CAT
GTC TTA TCT ACT ATC GTG GGA GCA ATG ATC whereby the smaller repetitive regions (cf. FIG. 3) in each gene above code for the peptides having fibronectin binding activity.

The invention further comprises a plasmid or phage comprising a nucleotide sequence coding for said fibronectin binding proteins.

The invention further comprises microorganisms containing at least one hydrid-DNA moLecule according to above. Such microorganisms have been deposited at the Deutsche Sammlung von Mikroorganismen under deposition number DSM 4614 (pSDF102) and DSM 4613 (pSDF203).

The invention further relates to a process for preparing fibronectin binding proteins comprising transfer of at least one hybrid-DNA molecule as set forth above into a microorganism, cultivating the said microorganism in a culture medium, and isolating the protein thus formed in a manner known per se.

A further aspect of the present invention comprises a chemical synthesis of the fibronectin binding proteins, whereby amino acids attach to form peptides in which the order of amino acids is based upon said nucleotide sequences encoding said proteins. The synthesis starts from the C-terminal glycine, and aspartic acid, respectively, which are reacted stepwise with the appropriate amino acid, whereby they are finally reacted with glutamic acid, and glutamic acid, respectively, at the N-terminal end to form of the fibronectin binding peptide regions.

Appropriate amino acids can also be fused to said amino acid sequence such as the IgG binding region of protein A. The invention will be described more in detail as follows with reference to the Examples given, however, without being restricted thereto.

EXAMPLE 1

Construction of a gene bank of chromosomal DNA from Streptococcus dysgalactiae

Chromosomal DNA from Streptococcus dysgalactiae, strain S2, was prepared in accordance with the perchlorate method (9). The DNA was partially cleaved using Sau 3AI, was size fractionated on a 1% agarose gel, and the DNA fragment within the size range 3 to 9 kb were collected, electro eluated, and purified on a Nensorb (Du Pont) column.

The plasmid vector pUC18 was cleaved using Bam HI and was phosphatase treated. The partially cleaved and fractionated streptococcus-DNA was ligated with the cleaved pUC18 vector. The ligation mixture was transformed to freeze competent E. coli, strain TG1, and was spread on LA plates containing ampicillin (50 µg/ml) and IPTG (0.1 mM), and 0.004% X-gal, called axi-plates. White colonies were transferred to LA plates with ampicillin (50 µg/mL).

Screening of a gene bank for a fibronectin binding protein (FNBP)

The white colonies from the axi plates were picked using tooth picks to LA plates with ampicillin, 52 colonies per plate. In total 728 transformants were collected. These were screened with regard to fibronectin binding activity using a filter assay method according to below.

Transformants are picked from an axi-plates to LA plates with ampicillin, and the plates are incubated over night. From these plates the colonies are replicated over to new LA plates, and which are incubated at 37° C. over night. A nitro-cellulose filter is put onto each agarplate with grown out colonies. When the filters are completely moistened the colonies are attached by suction and the filters are carefully removed. The filters are exposed to chloroform vapor for 5 min, and are then washed, 3×10 min, 37° C. in a buffer solution consisting of 100 mM Tris-HCl pH 7.5, 0.05% Tween-40, and 150 mM NaCl. The filters are allowed to dry at room temperature for about 30 min. The filters are preincubated in 150 mM NaCl, 10 mM Tris-HCl pH 7.5, and 1.4% fat free milk powder, for 2 hrs at 37° C., or room temperature over night. The milk powder buffer has to be freshly prepared. $^{125}$I labelled fibronectin is added (about 30,000 cpm per filter), and the filters are incubated at room temperature over night. The filters are washed, 3×10 min at 37° C. using a solution of 0.05% Tween-40, and 150 mM NaCl, whereupon the filters are dried. An unexposed film is put thereon, and is exposed for 3 to 5 days. The film is developed and the clones which have bound to $^{125}$I-fibronectin are identified and isolated.

The filter screening assay showed 3 positive clones, which all were further analysed. The fibronectin binding ability was further determined in a competition assay (10). Lysate of the E. coli clones were prepared by lysing the bacteria using lysozyme (1 mg/ml) in a buffer solution consisting of 100 mM Tris-HCl pH 7.5, 150 mM NaCl, and 1 mM EDTA. The fibronectin binding activity was analysed by determining the ability of the lysates to compete with S. aureus, strain Cowan I (alternatively strain 8325-4), and S. dysgalactiae, strain S2, respectively, with regard to their ability to bind to the $^{125}$I-labelled 29 kD fragment of fibronectin. The test showed that it is possible to drive out the fibronectin binding to the two staphylococcal strains, as well as strain S2 of S. dysgalactiae when using lysates of E. coli clones containing the strepto-cocci DNA. Inversely the binding of the 29 kD fragment of fibronectin to S. dysgalactiae can be inhibited by adding a lysate of E. coli clone containing a gene for fibronectin binding protein of S. aureus.

Restriction mapping and subcloning

Plasmid-DNA of the three positive subclones from the filter assay, called pSDF100, pSDF200, and pSDF300 were prepared using the LiCl method (11) and determined to be 4.9 kb, 6.9 kb, and 6.5 kb, respectively, by cleavages using restriction enzymes and analysis on agarose gels. All three clones were cleaved using about 20 of the most common restriction enzymes, which recognizes a sequence of 6 nucleotides and starting from cleavage pattern restriction maps were drafted. Two of the clones, pSDF100, and pSDF300, were partly overlapping having a 3.9 kb sequence in common, and thus only one was selected for further studies. As pSDF100 had a higher fibronectin binding activity than pSDF300 the former was selected.

pSDF100 and pSDF200 were subcloned in order to identify more closely the regions encoding fibronectin binding activity. pSDF100 was cleaved using Bam HI, whereupon the plasmid was religated. This clone with the Bam HI-Bam HI fragment deleted was called pSDF101 and was positive. pSDF101 was further cleaved using XbaI, which gave 3 fragments, one mainly consisting of the pUC18 vector. The other two XbaI-XbaI fragments were purified and inserted into the pUC18 vector. One of these fragments encodes fibronectin binding activity. This clone was called pSDF102. In the corresponding way subclones were constructed from pSDF200. The ClaI-SacI fragment deleted from pS6F200 gave a clone called pSDF201, and further the BglII-EcoRI fragment eliminated from pSDF201 gives pSDF202. Finally, the XhoI-EcoRI fragment has been deleted from pSDF20Z. This new clone was thereby obtained and was called pSDF203. All these new subclones are positive, i.e., they express fibronectin binding activity, cf. FIG. 1a and FIG. 1b.

Further subcloning by EcoIII digestion

In order to facilitate the nucleotide sequencing according to the dideoxymethod smaller subclones differing 150 to 200 base pairs in length are required in order to obtain overlapping DNA sequence. Exonucleas III digest one of the DNA strands from the 5' overhang, or from the blunt end, but leaves the 3' overhang. The single stranded DNA is then digested using S1-nuclease. This technique is used in the "Erase-a-Base" System Kit (Promega, Madison, USA) and makes it possible to construct series of subdlones which differs in some hundreds of nucleotides in size. In cases of interest the fibronectin binding activity was tested, cf. Table 1 below.

Table 1

Inhibition assay in tubes

Assay mixture: 100 μl of lysate of *E. coli* clones containing streptococcal DNA clones (the bacteria were grown on LB+50 μg ampicillin+1 mM IPTG, washed, and concentrated to $OD_{540}=5.0$)

100 μl Cowan I cells, heat killed, $OD_{540}=5.0$
100 μl $^{125}I$ labelled fibronectin, 8865 cpm
200 μl PBS+0.1% BSA
Incubation: 2 hrs, room temperature
Washing: Twice in PBS+0.1% BSA+0.05% Tween
The results are evident from Table 1 below.

| Lysate of subclone | Dilution of lysate | Number of cpm | % binding in relation to control without lysate |
|---|---|---|---|
| Control | Without lysate | 4430 | 100 |
| pSDF102c10 | undil | 550 | 12.4 |
|  | $10^{-2}$ | 3870 | 87.4 |
| pSDF102c13 | undil | 200 | 4.5 |
|  | $10^{-2}$ | 1440 | 32.5 |
| pSDF102c9 | undil | 610 | 13.8 |
|  | $10^{-2}$ | 3170 | 71.6 |
| pSDF102c11 | undil | 1400 | 31.6 |
|  | $10^{-2}$ | 3490 | 78.8 |
| pSDF102c14 | undil | 630 | 14.2 |
|  | $10^{-2}$ | 3220 | 72.7 |
| pSDF102c18 | undil | 4030 | 91.0 |
|  | $10^{-2}$ | 4300 | 97.1 |
| pSDF203c3 | undil | 640 | 14.4 |
|  | $10^{-2}$ | 2780 | 62.8 |
| pSDF203c6 | undil | 2710 | 61.2 |
|  | $10^{-2}$ | 4790 | 108 |
| pSDF203c8 | undil | 3180 | 71.8 |
|  | $10^{-2}$ | 3660 | 82.6 |
| pSDF203c11 | undil | 3540 | 79.9 |
|  | $10^{-2}$ | 3970 | 89.6 |
| pSDF203c15 | undil | 3860 | 87.1 |
|  | $10^{-2}$ | 4300 | 97.1 |
| pSDF203c9 | undil | 4020 | 90.7 |
|  | $10^{-2}$ | 4730 | 107 |
| pSDF102 | undil | 200 | 4.5 |
|  | $10^{-2}$ | 1050 | 23.7 |
| pSDF203 | undil | 180 | 4.1 |
|  | $10^{-2}$ | 950 | 21.4 |
| TG1 | undil | 3690 | 83.3 |

Nucleotide sequencing

Subclones obtained after an exoIII digestion and other subclones were sequenced using the dideoxy method according to Gem Seq$^R$ dsDNA Sequencing System (Promega Biotech., Madison, USA)

Nucleotide sequencing of pSDF102 gave the following sequence [SEQ ID NO:1]

CTA GAT ACC TCA GAA AAC AAA AAA TCT GTA ACT
GAA AAA GTA ATA ACT AGC GAT GTT AAA TAT
AAG ATT AAT GAT AAA GAA GTG AAA GGT AAA
GAA CTA GAC GAT GTC TCT TTA ACT TAC AGT
AAA GAA ACC GTT CGT AAG CCA CAG GTG GAA
CCA AAT GTT CCT GAT ACA CCT CAG GAA AAA
CCA TTG ACA CCG CTT GCA CCG TCA GAA CCT
TCA CAA CCA TCT ATT CCA GAG ACA CCA CTG
ATA CCG TCA GAA CCT TCA GTT CCA GAG ACA
TCA ACA CCA GAA GGT CCA ACA GAG GGA GAA
AAT AAT CTT GGT GGT CAG AGT GAA ATA ACG
ATT ACA GAA GAT TCT CAA TCA GGG ATG TCT
GGT CAA AAT CCT GGT TCT GGA AAT GAA ACA
GTG GTT
GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA
GAA GAT TCT AAA CCA AGT CAA GAG GAT GAG
GTG ATA ATC GGC GGT CAA GGT CAG GTG ATT
GAC TTT ACA GAA GAT ACT CAA TCT GGT ATG
TCT GGG GAT AAT AGC CAT ACA GAT GGG ACA
GTG CTT GAA
GAA GAC TCT AAA CCA AGT CAA GAG GAT GAG
GTG ATA ATC GGC GGT CAA GGT CAA GTG ATT
GAC TTT ACA GAA GAT ACC CAA ACC GGT ATG
TCT GGG
GCT GGA CAA GTA GAG AGT CCA ACA ACT ACC
GAA GAA ACC CAT AAA CCA GAA ATA ATC ATG

GGC GGT CAA AGT GAC CCT ATT GAT ATG GTT
GAG GAC ACT CTT CCT GGT ATG TCT GGC TCT
AAT GAA GCT ACT GTT GTG GAA GAA GAC ACA
CGT CCT AAA CTT CAA TTC CAT TTT GAT AAT
GAA GAG CCC GTT CCT GCA ACG GTT CCA ACC
GTT TCT CAA ACT CCT ATT GCT CAG GTA GAA
AGT AAA GTG CCT CAT GCC AAA GCA GAG AGT
GCG TTA CCT CAA ACT GGA GAT ACA AAT AAA
CTA GAA ACG TTC TTT ACC ATT ACA GCA CTA
ACT GTT ATT GGA GCG GCA GGA TTA CTA GGC
AAA AAA CGT CGT AAT AAT CAA ACT GAT TAA
TCA GCA GAT TTC ATC AAA CGC TAT AAA CAA
GGC TAA CAT TTT AGC CTT GTT TTA TAT TGT TTC
ACT GAC CTC TAA AAG TTA TGA CTG TTT TAA
AGG GGG GGT AGG CCA ATC CTC AAA AGT AGT
TAA GTT GAG AAA CAC CAC ATC ACT TTA GTC
TTA CTG CGC ATA CTA AAA GCA AAA GAT AAT
TAG GAG CAG TTG CTA ACT GGA AAA AAT CAA
ATG CAA AGC TAG TTG CCA AAG AAC TCT AGA whereby the repetitive domains of the sequence [SEQ ID NO:3]

GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA

GAA GAT TCT AAA CCA AGT CAA GAG GAT GAG
GTG ATA ATC GGC GGT CAA GGT CAG GTG ATT
GAC TTT ACA GAA GAT ACT CAA TCT GGT ATG
TCT GGG GAT AAT AGC CAT ACA GAT GGG ACA
GTG CTT GAA

GAA GAC TCT AAA CCA AGT CAA GAG GAT GAG
GTG ATA ATC GGC GGT CAA GGT CAA GTG ATT
GAC TTT ACA GAA GAT ACC CAA ACC GGT ATG
TCT GGG encode a peptide having fibronectin binding activity.

The nucleotide sequencing of pSDF203 gave the following sequence [SEQ ID NO:2]

CTC GAG GAA ACT TTG CCA AAC GAG GAA CAT
CAA TCA GGT GAT ACC ACA ACT ATT GAA GAT
ACT CGC CCG ATT GAT ACC ATG TCA GGT CTA
TCA GGA GAG ACT GGG CAG TCT GGT AAT ACT
ACA ATT GAG GAA GAT AGT ACG ACT CAC GTT
AAA TTC TCA AAA CGT GAT ATT AAT GGT AAA
GAA CTA GCA GGT GCT ATG ATT GAA CTA CGT
AAT CTA TCA GGT CAA ACT ATT CAA TCA TGG
ATA TCA GAC GGC ACA GTT AAA GTT TTC TAC
TTG ATG CCA GGG ACT TAT CAA TTT GTG GAG
ACG GCA GCG CCA GAA GGT TAT GAA TTG GCA
GCT CCA ATT ACC TTC ACA ATT GAT GAG AAA
GGA CAA ATT TGG GTA GAC AGT ACA ATT ACT
GAG GCG AGT CAA TCT ATT GAT TTC
GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC
GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT
GAG GAG AGC TTA CCA ACT GAA CAA GGC CAA
TCT GGC TCT ACA ACT GAA GTA GAA GAT
AGC AAG CCT AAA CTC TCT ATC CAC TTT GAT AAC
GAG TGG CCT AAG GAA GAC AAA CCA CAA CTA
CCT GCC GTT GAA AAA CCT AAG ACT AAG GAG
AGC TTG CCA GCC GCA GGG GAA GCT GAA CAT
GTC TTA TCT ACT ATC GTG GGA GCA ATG ATC whereby the repetitive domains of the sequence [SEQ ID NO:4]

GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC

GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT

GAG GAG AGC TTA CCA ACT GAA CAA GGC CAA
TCT GGC TCT ACA ACT GAA GTA GAA GAT encode a peptide having fibronectin binding activity.

Southern blot hybridisation detects no homologies on DNA level between the genes for the fibronectin binding protein of *S. aureus,* and the corresponding genes from *S. dysgalactiae.* The competitive inhibition between the proteins from the respective species depends most probably on the fact that their binding sites in the fibronectin within the $NH_2$ terminal 29 kD fragment are close to each other and thereby sterically block the binding.

Western blot analyses of lysate of the two fibronectin binding *E. coli* clones studied indicate using $^{125}I$ labelled fibronectin and autoradiography shows that subclone PSDF203 encodes a protein having a molecular weight of 70 kDa, and subclone pSDF102 a corresponding protein having a molecular weight of 110 kD.

The deduced amino acid sequences [SEQ ID NOS.:5 and 6] of the proteins or polypeptides from the above given nucleotide sequences encode for the following:

Glu Asp Thr Gln Thr Ser Gln Glu Asp Ile Val Leu Gly Gly Pro Gly Gln Val Ile Asp Phe Thr Glu Asp Ser Gln Pro Gly Met Ser Gly Asn Ser His Thr Ile Thr

Glu Asp Ser Lys Pro Ser Gln Glu Asp Glu Val Ile Gly Gly Gln Gly Gln Val Ile Asp Phe Thr Glu Asp Thr Gln Ser Gly Met Ser Gly Asp Asn Ser His Thr Asp Gly Thr Val Leu Glu

Glu Asp Ser Lys Pro Ser Gln Glu Asp Glu Val Ile Ile Gly Gly Gln Gly Gln Val Ile Asp Phe Thr Glu Asp Thr Gln Thr Gly Met Ser Gly and Glu Glu Thr Leu Pro Thr Glu Gln Gly Gln Ser Gly Ser Thr Thr Glu Val Glu Asp Thr Lys Gly Pro Glu Val Ile Ile Gly Gly Gln Gly Glu Ile Val Asp Ile Glu Glu Asn Leu pro Thr Glu Gln Gly Gln Ser Gly Ser Thr Thr Glu Val Glu Asp Thr Lys Gly pro Glu Val Ile Ile Gly Gly Gln Gly Glu Val Val Asp Ile Glu Glu Ser Leu Pro Thr Glu Gln Gly Gln Ser Gly Gly Ser Thr Thr Glu Val Glu Asp, respectively.

The present fibronectin binding proteins can be used in immunization, whereby the proteins, preferably in combination with a fusion protein in order to form a larger antigen to react upon, are injected in doses creating an immunological reaction in the host mammal. Thus the fibronectin binding proteins can be used in vaccination of rumens to mastitis created by streptococcal infections.

Further, the fibronectin binding proteins can be used to block an infection in an open skin lesion. Wounds can be treated by using a suspension comprising the fibronectin binding protein. Thus the fibronectin binding proteins can be used to treat wounds, e.g., for blocking bacterial binding sites in fibronectin, or for immunization (vaccination). In the latter case the host produces specific antibodies which can protect against attachment by bacterial strains comprising such fibronectin binding proteins. Hereby the antibodies block the adherence of the bacterial strains to damaged tissue.

Examples of colonizing of tissue damage are:

a) colonization and wounds in skin and connective tissue, which wounds have been caused by a mechanical trauma, chemical damage, and/or thermal damage;

b) colonizing of wounds on mucous membranes such as in the mouth cavity, or in the mammary glands, urethra or vagina;

c) colonizing of connective tissue proteins, which have been exposed by minimal tissue damage (micro lesions) in connection with epithelium and endothelium (mastitis, heart valve infection, hip exchange surgery).

When using the present fibronectin binding proteins, prepared by means of hybrid-DNA technique, or synthesized, for immunization (vaccination) in mammals, including humans, the proteins, or polypeptides are dispersed in sterile isotonic saline solution, optionally while adding a pharmaceutically acceptable dispersing agent. Different types of adjuvants can further be used in order to sustain the release in the tissue, and thus expose the protein for a longer period of time to the immuno defence system of a body.

A suitable dose to obtain immunization is 0.5 to 5 µg of fibronectin binding protein per kg body weight and injection at immunization. In order to obtain durable immunization, vaccinations should be carried out at consecutive occasions with an interval of 1 to 3 weeks, preferably at three occasions. Adjuvants are normally not added when repeating the immunization treatment.

When using the present fibronectin binding proteins or polypeptides for local topical administration the protein is dispersed in an isotonic saline solution to a concentration of 25 to 250 µg per ml. The wounds are then treated with such an amount only to obtain a complete wetting of the wound surface. For an average wound thus only a couple of milliliters of solution are used in this way. After treatment using the protein solution the wounds are suitably washed with isotonic saline solution or another suitable wound treatment solution.

Further the fibronectin binding protein, or synthetized polypeptide of the present invention can be used to diagnose bacterial infections caused by *S. dysgalactiae* strains, whereby a fibronectin binding protein of the present invention is immobilized on a solid carrier, such as small Latex or Sepharose$^R$ beads, whereupon sera containing antibodies are allowed to pass and react with the fibronectin binding protein thus immobilized. The agglutination is then measured by known methods.

Further the fibronectin binding protein or polypeptide can be used in an ELISA test (Enzyme Linked Immuno Sorbent Assay; E Engvall, Med. Biol. 55, 193 (1977)). Hereby wells in a polystyrene microtitre plate are coated with the fibronectin binding protein and incubated over night at 4° C. The plates are then thoroughly washed using PBS containing 0.05% Tween 20, and dried. Serial dilutions of the patient serum made in PBS-Tween, are added to the wells, and are incubated at 30° C. for 1.5 hrs. After rinsing anti-human IgG conjugated with an enzyme, or a horseradish peroxidase, or an alkaline phosphatase is added to the wells and further incubated at 30° C. for 1.5 hrs. During these incubations IgG from patient serum, and added antihuman IgG-enzyme conjugate, respectively, has been bound thereto. After rinsing, an enzyme substrate is added, p-nitrophosphate in case of an alkaline phosphatase, or orthophenylene diamine substrate (OPD) in case of a peroxidase has been used, respectively. The wells of the plates are then rinsed using a citrate buffer containing 0.055% OPD, and 0.005% $H_2O_2$, and incubated at 30° C. for 10 min. The enzyme reaction is stopped by adding a 4N solution of $H_2SO_4$ to each well. The color development is measured using a spectrophotometer.

Depending on the type of enzyme substrate used a fluoroscence measurement can be used as well.

Another method to diagnose *S. dysgalactiae* infections is by using the DNA gene probe method based on the nucleotide sequence for the fibronectin binding protein or part thereof. Thereby the natural or synthetic DNA sequence is attached to a solid carrier, such as a nitrocellulose filter, a nylon filter, or a polystyrene plate as mentioned above, by e.g., adding milk in the case of diagnosing mastitis, to the surface. The DNA gene probe, optionally labelled enzymatically, or by a radioactive isotope, is then added to the solid surface plate comprising the DNA sequence, whereby the DNA gene probe attaches to the membrane associated sequence where appearing. The enzyme or radioactive isotope can readily be determined by known methods.

The above the term fibronectin binding protein includes any of the polypeptide sequences as well, which constitute the minimal fibronectin binding site of the complete protein.

BRIEF DESCRIPTION OF THE DRAWINGS

FIGS. 1(*a* and *b*) Restriction map

A. Restriction map of the clone.

B. Different subclones constructed to determine the region in the gene which codes for fibronectin binding activity. The binding activity of the different gene products have been indicated.

Figure 1A:
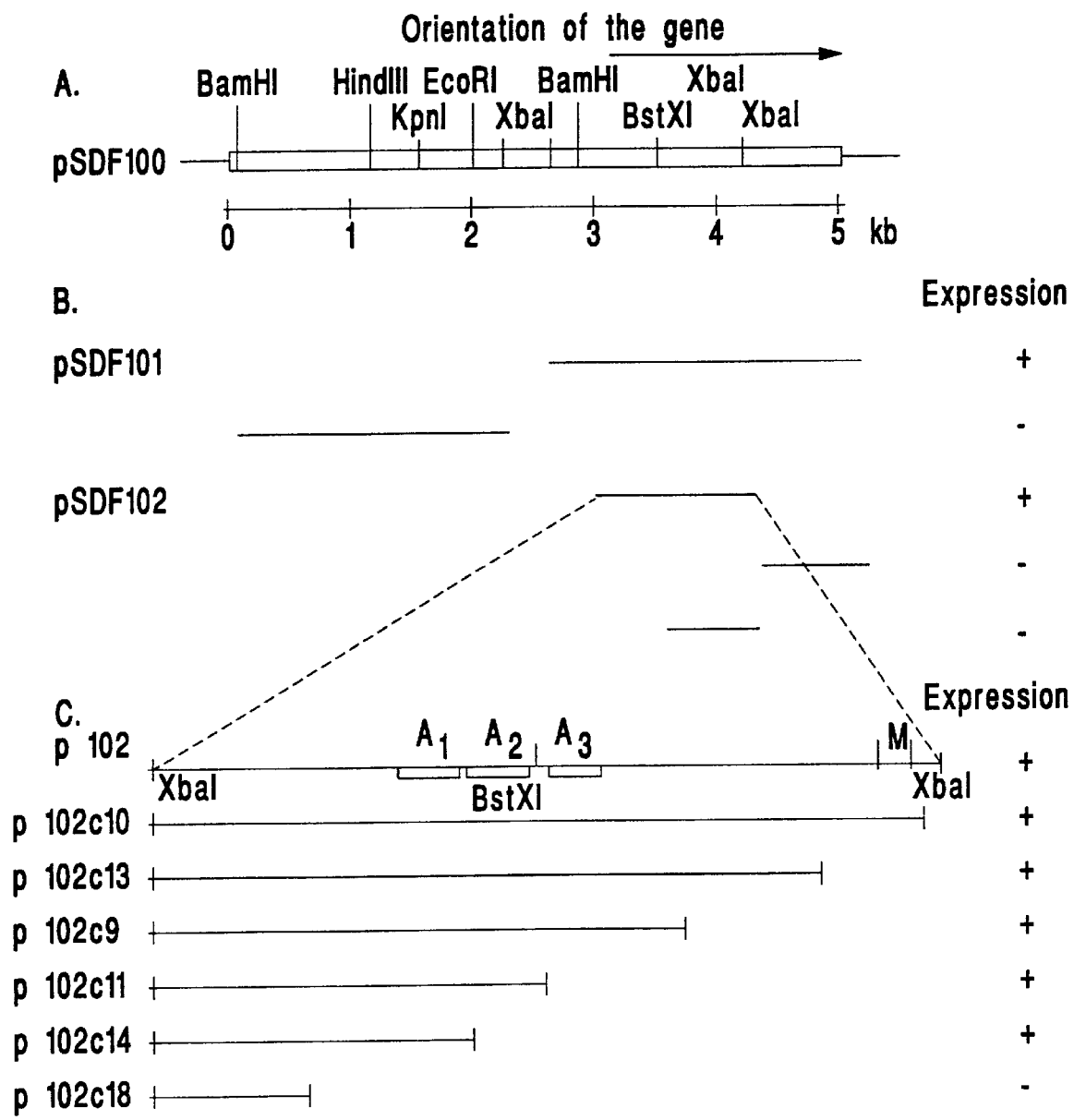
FIG. 1*a* (A–C). Restriction map and subclones of the 5 kb insert from *S. dysgalactiae* in the pUC18-vector called pSDF100.
Figure 1B:
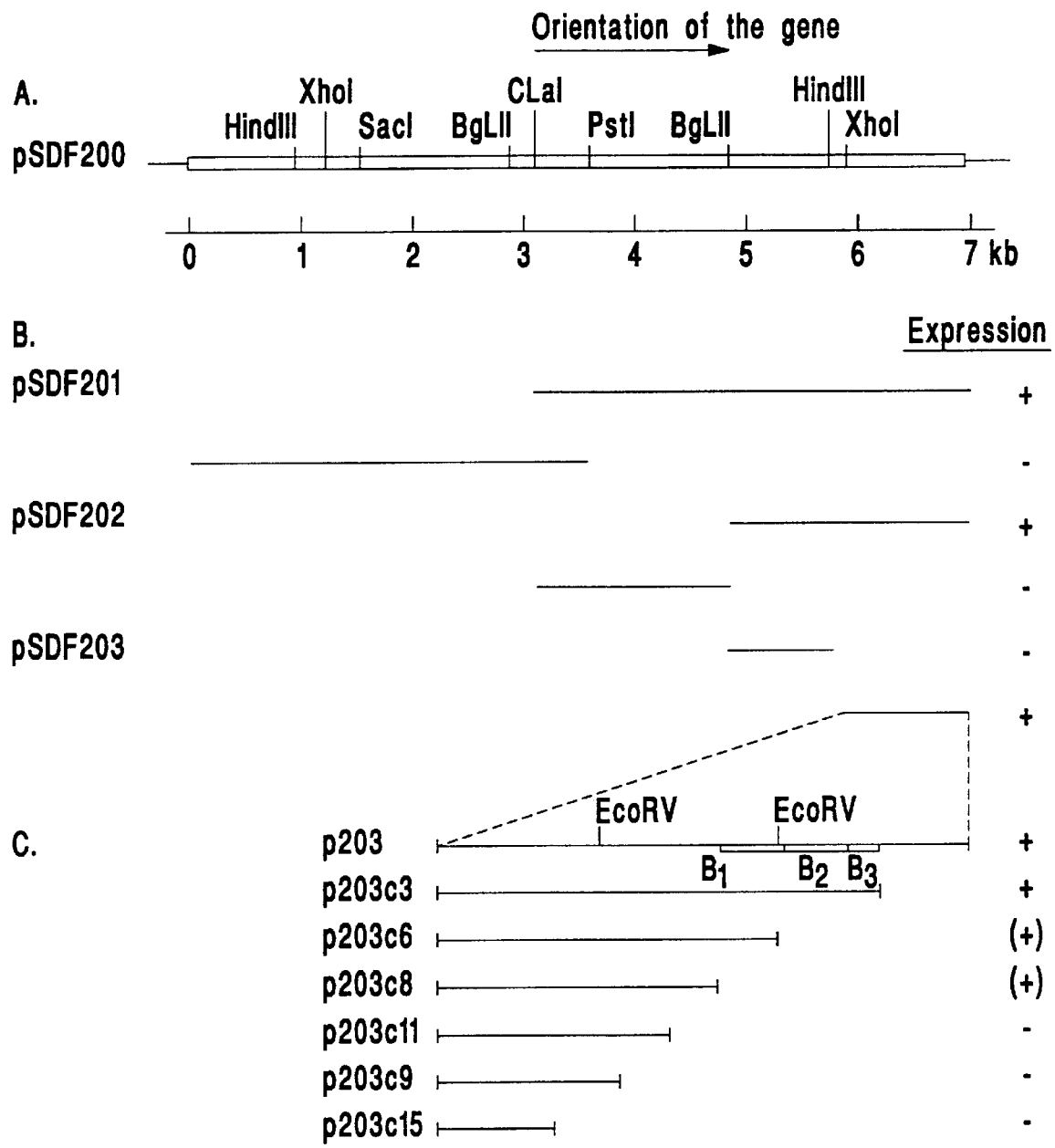
FIG. 1*b* (A–C). Restriction map and subclones of the 6.9 kb insert from *S. dysgalactiae* in the pUC18-vector called pSDF200.

C. Subclones obtained after digestion with ExoIII of pSDF102, and pSDF203, respectively. Scale: 1 cm=100 bp. M is the part of the DNA sequence which encodes the membrane associated part of the protein (=COOH-terminal). Subclone p102c10 contains the 3' end of the gene (FIG. 1*a*). $A_1$, $A_2$ och $A_3$, and $B_1$, $B_2$, and $B_3$, respectively, denote repetitive domains of the sequences [SEQ ID NOS:7 and 8] (cf. FIG. 3)

Figure 2:
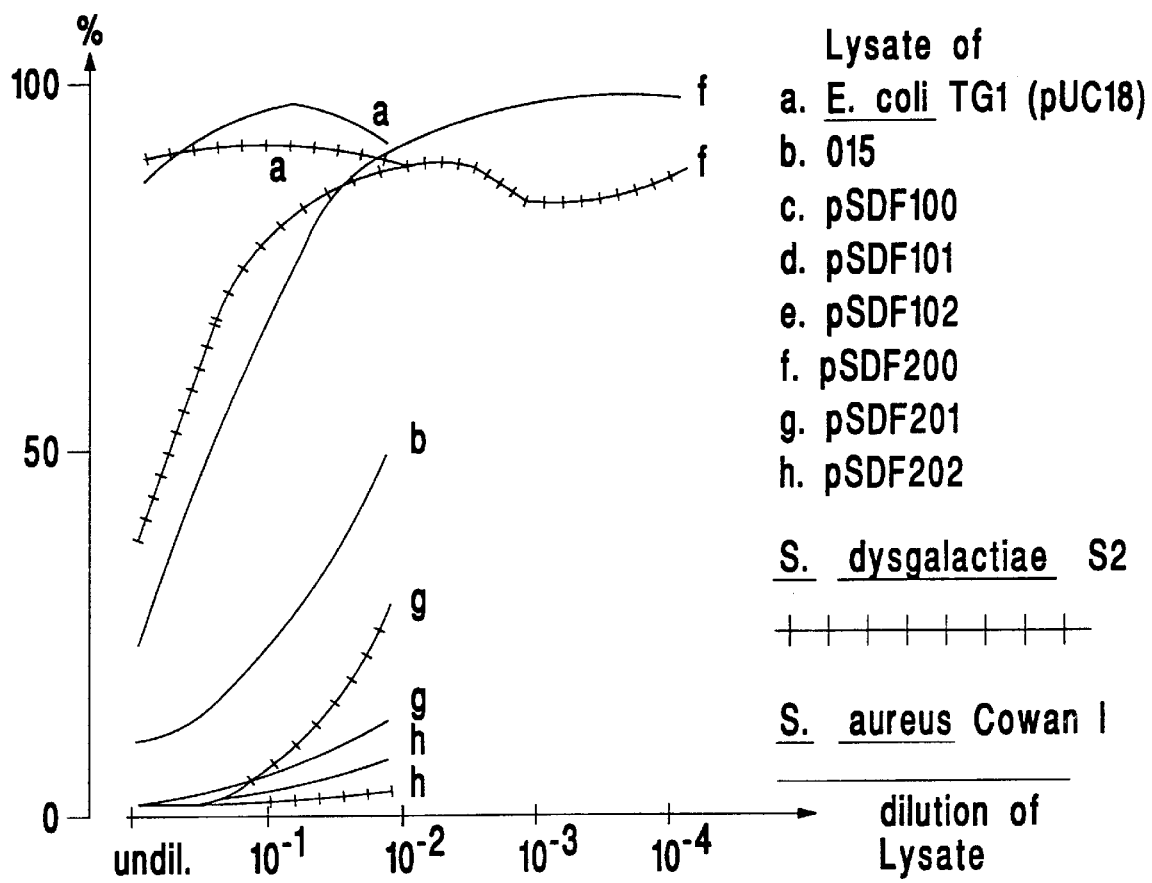

FIG. 2 Inhibition assay in tubes

Binding of $^{125}I$ labelled fibronectin to cells of *S. dysgalactiae* S2, and *S. aureus* Cowan I, respectively, at the addition of Lysates of *E. coli*-clones. The percentage values given are related to the binding of $^{125}I$ labelled fibronectin to cells in the absence of lysate. As a negative control a lysate of *E. coli* TG1 with pUC18-vector without insert was used, which had no influence on the binding of the cells to fibronectin. *E. coli* clone 015 contains a gene from *S. aureus* encoding for fibronectin binding activity.

FIGS. 3(A and B) shows repetitive sequences [SEQ ID NOS:7 and 8] of pSDF102 and pSDF203.

FIG. 4 [SEQ ID NO:9] shows the nucleotide and deduced amino acid sequences of pSDF102.

FIG. 5 [SEQ ID NO:10] shows the nucleotide and deduced amino acid sequences of pSDF203.

References

1. Hymes, R. O. (1985) Annu. Rev. Cell Biol. 1, 67–90.
2. Kuusela, P. (1978) Nature 276, 718–720.
3. Switalski, L. et al (1982) Eur. J. Clin. Microbiol. 1, 381–387.

4. Fröman, G. et al. (1984) J. Biol. Chem. 259, 14899–14905.
5. Baloda, S. B. et al (1985) FEMS Microbiol. Lett. 28, 1–5.
6. Wadström, T. et al (1985) In Jackson, G. J. (ed), Pathogenesis of Infection, Springer Verlag, Berlin, Heidelberg, New York, Tokyo, pp. 193–207.
7. Lopes, J. D. et al (1985) Science 229, 275–277.
8. Langone, I. I. (1982) Adv. Immunol. 32, 157–252.
9. Marmur, J. (1961) J. Mol. Biol. 3, 208–218.
10. Flock, J.-I. et al (1987) The EMBO Journal 6, 2351–2357.
11. Monstein, H.-J. et al (1986) Biochem. Int. 12, 889–896.

We claim:

1. A pharmaceutical composition comprising a protein or polypeptide having fibronectin binding properties and a pharmaceutically acceptable carrier therefor, wherein said protein or polypeptide comprises at least one amino acid sequence selected from the group consisting of:

Glu Asp Thr Gln Thr Ser Gln Glu Asp Ile Val Leu Gly Gly Pro Gly Gln Val Ile Asp Phe Thr Glu Asp Ser Gln Pro Gly Met Ser Gly Asn Ser His Thr Ile Thr

Glu Asp Ser Lys Pro Ser Gln Glu Asp Glu Val Ile Ile Gly Gly Gln Gly Gln Val Ile Asp Phe Thr Glu Asp Thr Gln Ser Gly Met Ser Gly Asp Asn Ser His Thr Asp Gly Thr Val Leu Glu

Glu Asp Ser Lys Pro Ser Gln Glu Asp Glu Val Ile Ile Gly Gly Gln Gly Gln Val Ile Asp Phe Thr Glu Asp Thr Gln Thr Gly Met Ser Gly (SEQ ID NO: 5)

and

Glu Glu Thr Leu Pro Thr Glu Gln Gly Gln Ser Gly Ser Thr Thr Glu Val Glu Asp Thr Lys Gly Pro Glu Val Ile Ile Gly Gly Gln Gly Glu Ile Val Asp Ile

Glu Glu Asn Leu Pro Thr Glu Gln Gly Gln Ser Gly Ser Thr Thr Glu Val Glu Asp Thr Lys Gly Pro Glu Val Ile Ile Gly Gly Gln Gly Glu Val Val Asp Ile

Glu Glu Ser Leu Pro Thr Glu Gln Gly Gln Ser Gly Gly Ser Thr Thr Glu Val Glu Asp (SEQ ID NO: 6).

2. A method of preventing infections caused by *S. dysgalactiae* in a mammal, said method comprising administering a prophylactically effective amount of the pharmaceutical composition of claim 1 to a mammal in need of such treatment.

3. A method for the treatment of infections caused by *S. dysgalactiae* in mammals comprising administering a therapeutically active amount of at least one fibronectin binding protein or polypeptide comprising at least one amino acid sequence selected from the group consisting of:

Glu Asp Thr Gln Thr Ser Gln Glu Asp Ile Val Leu Gly Gly Pro Gly Gln Val Ile Asp Phe Thr Glu Asp Ser Gln Pro Gly Met Ser Gly Asn Ser His Thr Ile Thr

Glu Asp Ser Lys Pro Ser Gln Glu Asp Glu Val Ile Ile Gly Gly Gln Gly Gln Val Ile Asp Phe Thr Glu Asp Thr Gln Ser Gly Met Ser Gly Asp Asn Ser His Thr Asp Gly Thr Val Leu Glu

Glu Asp Ser Lys Pro Ser Gln Glu Asp Glu Val Ile Ile Gly Gly Gln Gly Gln Val Ile Asp Phe Thr Glu Asp Thr Gln Thr Gly Met Ser Gly (SEQ ID NO: 5)

and

Glu Glu Thr Leu Pro Thr Glu Gln Gly Gln Ser Gly Ser Thr Thr Glu Val Glu Asp Thr Lys Gly Pro Glu Val Ile Ile Gly Gly Gln Gly Glu Ile Val Asp Ile

Glu Glu Asn Leu Pro Thr Glu Gln Gly Gln Ser Gly Ser Thr Thr Glu Val Glu Asp Thr Lys Gly Pro Glu Val Ile Ile Gly Gly Gln Gly Glu Val Val Asp Ile

Glu Glu Ser Leu Pro Thr Glu Gln Gly Gln Ser Gly Gly Ser Thr Thr Glu Val Glu Asp (SEQ ID NO: 6), optionally in combination with a pharmaceutically acceptable carrier or diluent.

4. A pharmaceutical composition which comprises at least one protein or polypeptide having fibronectin binding properties and a pharmaceutically acceptable carrier therefore, wherein said protein or polypeptide is encoded by a nucleotide sequence selected from the group consisting of:

CTA GAT ACC TCA GAA AAC AAA AAA TCT GTA ACT GAA AAA GTA ATA ACT AGC GAT GTT AAA

TAT AAG ATT AAT GAT AAA GAA GTG AAA GGT
AAA GAA CTA GAC GAT GTC TCT TTA ACT TAC
AGT AAA GAA ACC GTT CGT AAG CCA CAG
GTG GAA CCA AAT GTT CCT GAT ACA CCT CAG
GAA AAA CCA TTG ACA CCG CTT GCA CCG TCA
GAA CCT TCA CAA CCA TCT ATT CCA GAG ACA
CCA CTG ATA CCG TCA GAA CCT TCA GTT CCA
GAG ACA TCA ACA CCA GAA GGT CCA ACA
GAG GGA GAA AAT AAT CTT GGT GGT CAG AGT
GAA GAG ATA ACG ATT ACA GAA GAT TCT CAA
TCA GGG ATG TCT GGT CAA AAT CCT GGT TCT
GGA AAT GAA ACA GTG GTT

GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA

GAA GAT TCT AAA CCA AGT CAA GAG GAT GAG
GTG ATA ATC GGC GGT CAA GGT CAG GTG ATT
GAC TTT ACA GAA GAT ACT CAA TCT GGT ATG
TCT GGG GAT AAT AGC CAT ACA GAT GGG ACA
GTG CTT GAA

GAA GAC TCT AAA CCA AGT CAA GAG GAT GAG
GTG ATA ATC GGC GGT CAA GGT CAA CTG ATT
GAC TTT ACA GAA GAT ACC CAA ACC GGT ATG
TCT GGG

GCT GGA CAA GTA GAG AGT CCA ACA ACT ACC
GAA GAA ACC CAT AAA CCA GAA ATA ATC ATG
GGC GGT CAA AGT GAC CCT ATT GAT ATG GTT
GAG GAC ACT CTT CCT GGT ATG TCT GGC TCT
AAT GAA GCT ACT GTT GTG GAA GAA GAC
ACA CGT CCT AAA CTT CAA TTC CAT TTT GAT
AAT GAA GAG CCC GTT CCT GCA ACG GTT CCA
ACC GTT TCT CAA ACT CCT ATT GCT CAG GTA
GAA AGT AAA GTG CCT CAT GCC AAA GCA
GAG AGT GCG TTA CCT CAA ACT GGA GAT ACA
AAT AAA CTA GAA ACG TTC TTT ACC ATT ACA
GCA CTA ACT GTT ATT GGA GCG GCA GGA TTA
CTA GGC AAA AAA CGT CGT AAT AAT CAA ACT
GAT TTA TCA GCA GAT TTC ATC AAA CGC TAT
AAA CAA GGC TAA CAT TTT AGC CTT GTT TTA
TAT TGT TTC ACT GAC CTC TAA AAG TTA TGA
CTG TTT TAA AGG GGG GGT AGG CCA ATC CTC
AAA AGT AGT TAA GTT GAG AAA CAC CAC ATC
ACT TTA GTC TTA CTG CGC ATA CTA AAA GCA
AAA GAT AAT TAG GAG CAG TTG CTA ACT GGA
AAA AAT CAA ATG CAA AGC TAG TTG CCA AAG
AAC TCT AGA (SEQ ID NO: 9);

GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA

GAA GAT TCT AAA CCA AGT CAA GAG GAT GAG
GTG ATA ATC GGC GGT CAA GGT CAG GTG ATT
GAC TTT ACA GAA GAT ACT CAA TCT GGT ATG
TCT GGG GAT AAT AGC CAT ACA GAT GGG ACA
GTG CTT GAA

GAA GAC TCT AAA CCA AGT CAA GAG GAT GAG
GTG ATA ATC GGC GGT CAA GGT CAA CTG ATT
GAC TTT ACA GAA GAT ACC CAA ACC GGT ATG
TCT GGG (SEQ ID NO: 3);

CTC GAG GAA ACT TTG CCA AAC GAG GAA CAT
CAA TCA GGT GAT ACC ACA ACT ATT GAA GAT
ACT CGC CCG ATT GAT ACC ATG TCA GGT CTA
TCA GGA GAG ACT GGG CAG TCT GGT AAT ACT
ACA ATT GAG GAA GAT AGT ACG ACT CAC GTT
AAA TTC TCA AAA CGT GAT ATT AAT GGT AAA

GAA CTA GCA GGT GCT ATG ATT GAA CTA CGT
AAT CTA TCA GGT CAA ACT ATT CAA TCA TGG
ATA TCA GAC GGC ACA GTT AAA GTT TTC TAC
TTG ATG CCA GGG ACT TAT CAA TTT GTG GAG
ACG GCA GCG CCA GAA GGT TAT GAA TTG
GCA GCT CCA ATT ACC TTC ACA ATT GAT GAG
AAA GGA CAA ATT TGG GTA GAC AGT ACA ATT
ACT GAG GCG AGT CAA TCT ATT GAT TTC

GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC

GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT

GAG GAG AGC TTA CCA ACT GAA CAA GGC CAA
TCT GGC TCT ACA ACT GAA GTA GAA GAT

AGC AAG CCT AAA CTC TCT ATC CAC TTT GAT
AAC GAG TGG CCT AAG GAA GAC AAA CCA
CAA CTA CCT GCC GTT GAA AAA CCT AAG ACT
AAG GAG AGC TTG CCA GCC GCA GGG GAA
GCT GAA CAT GTC TTA TCT ACT ATC GTG GGA
GCA ATG ATC (SEQ ID NO: 2); and GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT GAG GAG AGC TTA CCA ACT GAA CAA GGC CAA
TCT GGC TCT ACA ACT GAA GTA GAA GAT (SEQ
ID NO: 4).

5. A method of preventing infections caused by *S. dysgalactiae* in a mammal, said method comprising administering a prophylactically effective amount of the pharmaceutical composition of claim 4 to a mammal in need of such treatment.

6. A method for the treatment of infections caused by *S. dysgalactiae* in a mammal, said method comprising administering a therapeutically active amount of at least one fibronectin binding protein or polypeptide, wherein said protein or polypeptide is encoded by a nucleotide sequence selected from the group consisting of:

CTA GAT ACC TCA GAA AAC AAA AAA TCT GTA
ACT GAA AAA GTA ATA ACT AGC GAT GTT AAA
TAT AAG ATT AAT GAT AAA GAA GTG AAA GGT
AAA GAA CTA GAC GAT GTC TCT TTA ACT TAC
AGT AAA GAA ACC GTT CGT AAG CCA CAG
GTG GAA CCA AAT GTT CCT GAT ACA CCT CAG
GAA AAA CCA TTG ACA CCG CTT GCA CCG TCA
GAA CCT TCA CAA CCA TCT ATT CCA GAG ACA
CCA CTG ATA CCG TCA GAA CCT TCA GTT CCA
GAG ACA TCA ACA CCA GAA GGT CCA ACA
GAG GGA GAA AAT AAT CTT GGT GGT CAG AGT
GAA GAG ATA ACG ATT ACA GAA GAT TCT CAA
TCA GGG ATG TCT GGT CAA AAT CCT GGT TCT
GGA AAT GAA ACA GTG GTT

GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA

GAA GAT TCT AAA CCA AGT CAA GAG GAT GAG
GTG ATA ATC GGC GGT CAA GGT CAG GTG ATT

GAC TTT ACA GAA GAT ACT CAA TCT GGT ATG
TCT GGG GAT AAT AGC CAT ACA GAT GGG ACA
GTG CTT GAA
GAA GAC TCT AAA CCA AGT CAA GAG GAT GAG
GTG ATA ATC GGC GGT CAA GGT CAA CTG ATT
GAC TTT ACA GAA GAT ACC CAA ACC GGT ATG
TCT GGG
GCT GGA CAA GTA GAG AGT CCA ACA ACT ACC
GAA GAA ACC CAT AAA CCA GAA ATA ATC ATG
GGC GGT CAA AGT GAC CCT ATT GAT ATG GTT
GAG GAC
ACT CTT CCT GGT ATG TCT GGC TCT AAT GAA
GCT ACT GTT GTG GAA GAA GAC ACA CGT CCT
AAA CTT CAA TTC CAT TTT GAT AAT GAA GAG
CCC GTT CCT GCA ACG GTT CCA ACC GTT TCT
CAA ACT CCT ATT GCT CAG GTA GAA AGT AAA
GTG CCT CAT GCC AAA GCA GAG AGT GCG TTA
CCT CAA ACT GGA GAT ACA AAT AAA CTA GAA
ACG TTC TTT ACC ATT ACA GCA CTA ACT GTT
ATT GGA GCG GCA GGA TTA CTA GGC AAA AAA
CGT CGT AAT AAT CAA ACT GAT TTA TCA GCA
GAT TTC ATC AAA CGC TAT AAA CAA GGC TAA
CAT TTT AGC CTT GTT TTA TAT TGT TTC ACT
GAC CTC TAA AAG TTA TGA CTG TTT TAA AGG
GGG GGT AGG CCA ATC CTC AAA AGT AGT TAA
GTT GAG AAA CAC CAC ATC ACT TTA GTC TTA
CTG CGC ATA CTA AAA GCA AAA GAT AAT TAG
GAG CAG TTG CTA ACT GGA AAA AAT CAA ATG
CAA AGC TAG TTG CCA AAG AAC TCT AGA
(SEQ ID NO: 9);
GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA
GAA GAT TCT AAA CCA AGT CAA GAG GAT GAG
GTG ATA ATC GGC GGT CAA GGT CAG GTG ATT
GAC TTT ACA GAA GAT ACT CAA TCT GGT ATG
TCT GGG GAT AAT AGC CAT ACA GAT GGG ACA
GTG CTT GAA
GAA GAC TCT AAA CCA AGT CAA GAG GAT GAG
GTG ATA ATC GGC GGT CAA GGT CAA CTG ATT
GAC TTT ACA GAA GAT ACC CAA ACC GGT ATG
TCT GGG (SEQ ID NO: 3);
CTC GAG GAA ACT TTG CCA AAC GAG GAA CAT
CAA TCA GGT GAT ACC ACA ACT ATT GAA GAT
ACT CGC CCG ATT GAT ACC ATG TCA GGT CTA
TCA GGA GAG ACT GGG CAG TCT GGT AAT ACT
ACA ATT GAG GAA GAT AGT ACG ACT CAC GTT
AAA TTC TCA AAA CGT GAT ATT AAT GGT AAA
GAA CTA GCA GGT GCT ATG ATT GAA CTA CGT
AAT CTA TCA GGT CAA ACT ATT CAA TCA TGG
ATA TCA GAC GGC ACA GTT AAA GTT TTC TAC
TTG ATG CCA GGG ACT TAT CAA TTT GTG GAG
ACG GCA GCG CCA GAA GGT TAT GAA TTG
GCA GCT CCA ATT ACC TTC ACA ATT GAT GAG
AAA GGA CAA ATT TGG GTA GAC AGT ACA ATT
ACT GAG GCG AGT CAA TCT ATT GAT TTC
GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC
GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT
GAG GAG AGC TTA CCA ACT GAA CAA GGC CAA
TCT GGC TCT ACA ACT GAA GTA GAA GAT

AGC AAG CCT AAA CTC TCT ATC CAC TTT GAT
AAC GAG TGG CCT AAG GAA GAC AAA CCA
CAA CTA CCT GCC GTT GAA AAA CCT AAG ACT
AAG GAG AGC TTG CCA GCC GCA GGG GAA
GCT GAA CAT GTC TTA TCT ACT ATC GTG GGA
GCA ATG ATC (SEQ ID NO: 2); and
GAG GAA ACT TTA CCA ACT GAA CAA GGC CAA
TCT GGC TCT ACA ACG GAG GTT GAG GAT ACT
AAA GGC CCA GAA GTC ATT ATC GGC GGT CAG
GGA GAG ATT GTT GAT ATC
GAG GAG AAC TTA CCA ACT GAA CAA GGC CAA
TCT GGC TCT ACA ACT GAA GTA GAG GAT ACT
AAA GGC CCA GAA GTC ATT ATC GGC GGT CAA
GGA GAG GTT GTT GAT ATT
GAG GAG AGC TTA CCA ACT GAA CAA GGC CAA
TCT GGC TCT ACA ACT GAA GTA GAA GAT (SEQ
ID NO: 4)
together with a pharmaceutically acceptable diluent or carrier.

7. A composition of matter comprising at least one protein or polypeptide isolated from *S. dysgalactiae* and having fibronectin binding properties, and a carrier therefor, wherein said protein or polypeptide comprises at least one amino acid sequence selected from the group consisting of:

Glu Asp Thr Gln Thr Ser Gln Glu Asp Ile Val Leu Gly Gly
Pro Gly Gln Val Ile Asp Phe Thr Glu Asp Ser Gln Pro
Gly Met Ser Gly Asn Ser His Thr Ile Thr

Glu Asp Ser Lys Pro Ser Gln Glu Asp Glu Val Ile Ile Gly
Gly Gln Gly Gln Val Ile Asp Phe Thr Glu Asp Thr Gln
Ser Gly Met Ser Gly Asp Asn Ser His Thr Asp Gly Thr
Val Leu Glu

Glu Asp Ser Lys Pro Ser Gln Glu Asp Glu Val Ile Ile Gly
Gly Gln Gly Gln Val Ile Asp Phe Thr Glu Asp Thr Gln
Thr Gly Met Ser Gly (SEQ ID NO: 5); and Glu Glu Thr Leu Pro Thr Glu Gln Gly Gln Ser Gly Ser Thr
Thr Glu Val Glu Asp Thr Lys Gly Pro Glu Val Ile Ile
Gly Gly Gln Gly Glu Ile Val Asp Ile Glu Glu Asn Leu Pro Thr Glu Gln Gly Gln Ser Gly Ser
Thr Thr Glu Val Glu Asp Thr Lys Gly Pro Glu Val Ile
Ile Gly Gly Gln Gly Glu Val Val Asp Ile Glu Glu Ser Leu Pro Thr Glu Gln Gly Gln Ser Gly Gly
Ser Thr Thr Glu Val Glu Asp (SEQ ID NO: 6).

8. A composition of matter comprising at least one protein or polypeptide isolated from *S. dysealactiae* and having fibronectin binding properties and a carrier therefor wherein said protein or polypeptide is encoded by a nucleotide sequence selected from the group consisting of:

CTA GAT ACC TCA GAA AAC AAA AAA TCT GTA
ACT GAA AAA GTA ATA ACT AGC GAT GTT AAA
TAT AAG ATT AAT GAT AAA GAA GTG AAA GGT
AAA GAA CTA GAC GAT GTC TCT TTA ACT TAC
AGT AAA GAA ACC GTT CGT AAG CCA CAG
GTG GAA CCA AAT GTT CCT GAT ACA CCT CAG
GAA AAA CCA TTG ACA CCG CTT GCA CCG TCA
GAA CCT TCA CAA CCA TCT ATT CCA GAG ACA
CCA CTG ATA CCG TCA GAA CCT TCA GTT CCA
GAG ACA TCA ACA CCA GAA GGT CCA ACA
GAG GGA GAA AAT AAT CTT GGT GGT CAG AGT
GAA GAG ATA ACG ATT ACA GAA GAT TCT CAA
TCA GGG ATG TCT GGT CAA AAT CCT GGT TCT
GGA AAT GAA ACA GTG GTT
GAA GAC ACT CAA ACA AGT CAA GAG GAT ATT
GTA CTT GGT GGT CCA GGT CAA GTG ATT GAC
TTT ACA GAA GAT AGC CAA CCG GGT ATG TCT
GGT AAT AAT AGC CAT ACT ATT ACA

GAA GAT TCT AAA CCA AGT CAA GAG GAT GAG GTG ATA ATC GGC GGT CAA GGT CAG GTG ATT GAC TTT ACA GAA GAT ACT CAA TCT GGT ATG TCT GGG GAT AAT AGC CAT ACA GAT GGG ACA GTG CTT GAA

GAA GAC TCT AAA CCA AGT CAA GAG GAT GAG GTG ATA ATC GGC GGT CAA GGT CAA CTG ATT GAC TTT ACA GAA GAT ACC CAA ACC GGT ATG TCT GGG

GCT GGA CAA GTA GAG AGT CCA ACA ACT ACC GAA GAA ACC CAT AAA CCA GAA ATA ATC ATG GGC GGT CAA AGT GAC CCT ATT GAT ATG GTT GAG GAC ACT CTT CCT GGT ATG TCT GGC TCT AAT GAA GCT ACT GTT GTG GAA GAA GAC ACA CGT CCT AAA CTT CAA TTC CAT TTT GAT AAT GAA GAG CCC GTT CCT GCA ACG GTT CCA ACC GTT TCT CAA ACT CCT ATT GCT CAG GTA GAA AGT AAA GTG CCT CAT GCC AAA GCA GAG AGT GCG TTA CCT CAA ACT GGA GAT ACA AAT AAA CTA GAA ACG TTC TTT ACC ATT ACA GCA CTA ACT GTT ATT GGA GCG GCA GGA TTA CTA GGC AAA AAA CGT CGT AAT AAT CAA ACT GAT TTA TCA GCA GAT TTC ATC AAA CGC TAT AAA CAA GGC TAA CAT TTT AGC CTT GTT TTA TAT TGT TTC ACT GAC CTC TAA AAG TTA TGA CTG TTT AAA GGG GGT AGG CCA ATC CTC AAA AGT AGT TAA GTT GAG AAA CAC CAC ATC ACT TTA GTC TTA CTG CGC ATA CTA AAA GCA AAA GAT AAT TAG GAG CAG TTG CTA ACT GGA AAA AAT CAA ATG CAA AGC TAG TTG CCA AAG AAC TCT AGA (SEQ ID NO: 9);

GAA GAC ACT CAA ACA AGT CAA GAG GAT ATT GTA CTT GGT GGT CCA GGT CAA GTG ATT GAC TTT ACA GAA GAT AGC CAA CCG GGT ATG TCT GGT AAT AAT AGC CAT ACT ATT ACA

GAA GAT TCT AAA CCA AGT CAA GAG GAT GAG GTG ATA ATC GGC GGT CAA GGT CAG GTG ATT GAC TTT ACA GAA GAT ACT CAA TCT GGT ATG TCT GGG GAT AAT AGC CAT ACA GAT GGG ACA GTG CTT GAA

GAA GAC TCT AAA CCA AGT CAA GAG GAT GAG GTG ATA ATC GGC GGT CAA GGT CAA CTG ATT GAC TTT ACA GAA GAT ACC CAA ACC GGT ATG TCT GGG (SEQ ID NO: 3);

CTC GAG GAA ACT TTG CCA AAC GAG GAA CAT CAA TCA GGT GAT ACC ACA ACT ATT GAA GAT ACT CGC CCG ATT GAT ACC ATG TCA GGT CTA TCA GGA GAG ACT GGG CAG TCT GGT AAT ACT ACA ATT GAG GAA GAT AGT ACG ACT CAC GTT AAA TTC TCA AAA CGT GAT ATT AAT GGT AAA GAA CTA GCA GGT GCT ATG ATT GAA CTA CGT AAT CTA TCA GGT CAA ACT ATT CAA TCA TGG ATA TCA GAC GGC ACA GTT AAA GTT TTC TAC TTG ATG CCA GGG ACT TAT CAA TTT GTG GAG ACG GCA GCG CCA GAA GGT TAT GAA TTG GCA GCT CCA ATT ACC TTC ACA ATT GAT GAG AAA GGA CAA ATT TGG GTA GAC AGT ACA ATT ACT GAG GCG AGT CAA TCT ATT GAT TTC

GAG GAA ACT TTA CCA ACT GAA CAA GGC CAA TCT GGC TCT ACA ACG GAG GTT GAG GAT ACT AAA GGC CCA GAA GTC ATT ATC GGC GGT CAG GGA GAG ATT GTT GAT ATC

GAG GAG AAC TTA CCA ACT GAA CAA GGC CAA TCT GGC TCT ACA ACT GAA GTA GAG GAT ACT AAA GGC CCA GAA GTC ATT ATC GGC GGT CAA GGA GAG GTT GTT GAT ATT

GAG GAG AGC TTA CCA ACT GAA CAA GGC CAA TCT GGC TCT ACA ACT GAA GTA GAA GAT

AGC AAG CCT AAA CTC TCT ATC CAC TTT GAT AAC GAG TGG CCT AAG GAA GAC AAA CCA CAA CTA CCT GCC GTT GAA AAA CCT AAG ACT AAG GAG AGC TTG CCA GCC GCA GGG GAA GCT GAA CAT GTC TTA TCT ACT ATC GTG GGA GCA ATG ATC (SEQ ID NO: 2);

and

GAG GAA ACT TTA CCA ACT GAA CAA GGC CAA TCT GGC TCT ACA ACG GAG GTT GAG GAT ACT AAA GGC CCA GAA GTC ATT ATC GGC GGT CAG GGA GAG ATT GTT GAT ATC

GAG GAG AAC TTA CCA ACT GAA CAA GGC CAA TCT GGC TCT ACA ACT GAA GTA GAG GAT ACT AAA GGC CCA GAA GTC ATT ATC GGC GGT CAA GGA GAG GTT GTT GAT ATT

GAG GAG AGC TTA CCA ACT GAA CAA GGC CAA TCT GGC TCT ACA ACT GAA GTA GAA GAT (SEQ ID NO: 4).

9. A composition of matter comprising at least one recombinantly produced protein or polypeptide having fibronectin binding properties, and a carrier therefor, wherein said protein or polypeptide comprises at least one amino acid sequence selected from the group consisting of:

Glu Asp Thr Gln Thr Ser Gln Glu Asp Ile Val Leu Gly Gly Pro Gly Gln Val Ile Asp Phe Thr Glu Asp Ser Gln Pro Gly Met Ser Gly Asn Ser His Thr Ile Thr

Glu Asp Ser Lys Pro Ser Gln Glu Asp Glu Val Ile Ile Gly Gly Gln Gly Gln Val Ile Asp Phe Thr Glu Asp Thr Gln Ser Gly Met Ser Gly Asp Asn Ser His Thr Asp Gly Thr Val Leu Glu

Glu Asp Ser Lys Pro Ser Gln Glu Asp Glu Val Ile Ile Gly Gly Gln Gly Gln Val Ile Asp Phe Thr Glu Asp Thr Gln Thr Gly Met Ser Gly (SEQ ID NO: 5); and Glu Glu Thr Leu Pro Thr Glu Gln Gly Gln Ser Gly Ser Thr Thr Glu Val Glu Asp Thr Lys Gly Pro Glu Val Ile Ile Gly Gly Gln Gly Glu Ile Val Asp Ile Glu Glu Asn Leu Pro Thr Glu Gln Gly Gln Ser Gly Ser Thr Thr Glu Val Glu Asp Thr Lys Gly Pro Glu Val Ile Ile Gly Gly Gln Gly Glu Val Val Asp Ile Glu Glu Ser Leu Pro Thr Glu Gln Gly Gln Ser Gly Gly Ser Thr Thr Glu Val Glu Asp (SEQ ID NO: 6).

10. A composition of matter comprising at least one recombinantly produced protein or polypeptide having fibronectin binding properties, and a carrier therefor, wherein said protein or polypeptide is encoded by a nucleotide sequence selected from the group consisting of:

CTA GAT ACC TCA GAA AAC AAA AAA TCT GTA ACT GAA AAA GTA ATA ACT AGC GAT GTT AAA TAT AAG ATT AAT GAT AAA GAA GTG AAA GGT AAA GAA CTA GAC GAT GTC TCT TTA ACT TAC AGT AAA GAA ACC GTT CGT AAG CCA CAG GTG GAA CCA AAT GTT CCT GAT ACA CCT CAG GAA AAA CCA TTG ACA CCG CTT GCA CCG TCA GAA CCT TCA CAA CCA TCT ATT CCA GAG ACA CCA CTG ATA CCG TCA GAA CCT TCA GTT CCA GAG ACA TCA ACA CCA GAA GGT CCA ACA GAG GGA GAA AAT AAT CTT GGT GGT CAG AGT GAA GAG ATA ACG ATT ACA GAA GAT TCT CAA TCA GGG ATG TCT GGT CAA AAT CCT GGT TCT GGA AAT GAA ACA GTG GTT

GAA GAC ACT CAA ACA AGT CAA GAG GAT ATT GTA CTT GGT GGT CCA GGT CAA GTG ATT GAC TTT ACA GAA GAT AGC CAA CCG GGT ATG TCT GGT AAT AAT AGC CAT ACT ATT ACA

GAA GAT TCT AAA CCA AGT CAA GAG GAT GAG GTG ATA ATC GGC GGT CAA GGT CAG GTG ATT GAC TTT ACA GAA GAT ACT CAA TCT GGT ATG TCT GGG GAT AAT AGC CAT ACA GAT GGG ACA GTG CTT GAA

GAA GAC TCT AAA CCA AGT CAA GAG GAT GAG GTG ATA ATC GGC GGT CAA GGT CAA CTG ATT GAC TTT ACA GAA GAT ACC CAA ACC GGT ATG TCT GGG

GCT GGA CAA GTA GAG AGT CCA ACA ACT ACC GAA GAA ACC CAT AAA CCA GAA ATA ATC ATG GGC GGT CAA AGT GAC CCT ATT GAT ATG GTT GAG GAC ACT CTT CCT GGT ATG TCT GGC TCT AAT GAA GCT ACT GTT GTG GAA GAA GAC ACA CGT CCT AAA CTT CAA TTC CAT TTT GAT AAT GAA GAG CCC GTT CCT GCA ACG GTT CCA ACC GTT TCT CAA ACT CCT ATT GCT CAG GTA GAA AGT AAA GTG CCT CAT GCC AAA GCA GAG AGT GCG TTA CCT CAA ACT GGA GAT ACA AAT AAA CTA GAA ACG TTC TTT ACC ATT ACA GCA CTA ACT GTT ATT GGA GCG GCA GGA TTA CTA GGC AAA AAA CGT CGT AAT AAT CAA ACT GAT TTA TCA GCA GAT TTC ATC AAA CGC TAT AAA CAA GGC TAA CAT TTT AGC CTT GTT TTA TAT TGT TTC ACT GAC CTC TAA AAG TTA TGA CTG TTT TAA AGG GGG GGT AGG CCA ATC CTC AAA AGT AGT TAA GTT GAG AAA CAC CAC ATC ACT TTA GTC TTA CTG CGC ATA CTA AAA GCA AAA GAT AAT TAG GAG CAG TTG CTA ACT GGA AAA AAT CAA ATG CAA AGC TAG TTG CCA AAG AAC TCT AGA (SEQ ID NO: 9);

GAA GAC ACT CAA ACA AGT CAA GAG GAT ATT GTA CTT GGT GGT CCA GGT CAA GTG ATT GAC TTT ACA GAA GAT AGC CAA CCG GGT ATG TCT GGT AAT AAT AGC CAT ACT ATT ACA

GAA GAT TCT AAA CCA AGT CAA GAG GAT GAG GTG ATA ATC GGC GGT CAA GGT CAG GTG ATT GAC TTT ACA GAA GAT ACT CAA TCT GGT ATG TCT GGG GAT AAT AGC CAT ACA GAT GGG ACA GTG CTT GAA

GAA GAC TCT AAA CCA AGT CAA GAG GAT GAG GTG ATA ATC GGC GGT CAA GGT CAA CTG ATT GAC TTT ACA GAA GAT ACC CAA ACC GGT ATG TCT GGG (SEQ ID NO: 3);

CTC GAG GAA ACT TTG CCA AAC GAG GAA CAT CAA TCA GGT GAT ACC ACA ACT ATT GAA GAT ACT CGC CCG ATT GAT ACC ATG TCA GGT CTA TCA GGA GAG ACT GGG CAG TCT GGT AAT ACT ACA ATT GAG GAA GAT AGT ACG ACT CAC GTT AAA TTC TCA AAA CGT GAT ATT AAT GGT AAA GAA CTA GCA GGT GCT ATG ATT GAA CTA CGT AAT CTA TCA GGT CAA ACT ATT CAA TCA TGG ATA TCA GAC GGC ACA GTT AAA GTT TTC TAC TTG ATG CCA GGG ACT TAT CAA TTT GTG GAG ACG GCA GCG CCA GAA GGT TAT GAA TTG GCA GCT CCA ATT ACC TTC ACA ATT GAT GAG AAA GGA CAA ATT TGG GTA GAC AGT ACA ATT ACT GAG GCG AGT CAA TCT ATT GAT TTC

GAG GAA ACT TTA CCA ACT GAA CAA GGC CAA TCT GGC TCT ACA ACG GAG GTT GAG GAT ACT AAA GGC CCA GAA GTC ATT ATC GGC GGT CAG GGA GAG ATT GTT GAT ATC

GAG GAG AAC TTA CCA ACT GAA CAA GGC CAA TCT GGC TCT ACA ACT GAA GTA GAG GAT ACT AAA GGC CCA GAA GTC ATT ATC GGC GGT CAA GGA GAG GTT GTT GAT ATT

GAG GAG AGC TTA CCA ACT GAA CAA GGC CAA TCT GGC TCT ACA ACT GAA GTA GAA GAT

AGC AAG CCT AAA CTC TCT ATC CAC TTT GAT AAC GAG TGG CCT AAG GAA GAC AAA CCA CAA CTA CCT GCC GTT GAA AAA CCT AAG ACT AAG GAG AGC TTG CCA GCC GCA GGG GAA GCT GAA CAT GTC TTA TCT ACT ATC GTG GGA GCA ATG ATC (SEQ ID NO: 2);

and

GAG GAA ACT TTA CCA ACT GAA CAA GGC CAA TCT GGC TCT ACA ACG GAG GTT GAG GAT ACT AAA GGC CCA GAA GTC ATT ATC GGC GGT CAG GGA GAG ATT GTT GAT ATC

GAG GAG AAC TTA CCA ACT GAA CAA GGC CAA TCT GGC TCT ACA ACT GAA GTA GAG GAT ACT AAA GGC CCA GAA GTC ATT ATC GGC GGT CAA GGA GAG GTT GTT GAT ATT

GAG GAG AGC TTA CCA ACT GAA CAA GGC CAA TCT GGC TCT ACA ACT GAA GTA GAA GAT (SEQ ID NO: 4).

* * * * *